(12) United States Patent
Keller

(10) Patent No.: US 10,285,669 B2
(45) Date of Patent: May 14, 2019

(54) BIOPSY SAMPLE CONTAINER

(71) Applicant: Devicor Medical Products, Inc., Cincinnati, OH (US)

(72) Inventor: Bryan R. Keller, Loveland, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days.

(21) Appl. No.: 15/638,740

(22) Filed: Jun. 30, 2017

(65) Prior Publication Data

US 2018/0000463 A1    Jan. 4, 2018

Related U.S. Application Data

(60) Provisional application No. 62/357,474, filed on Jul. 1, 2016, provisional application No. 62/406,486, filed on Oct. 11, 2016.

(51) Int. Cl.
*G01N 1/00* (2006.01)
*A61B 10/00* (2006.01)
(Continued)

(52) U.S. Cl.
CPC ...... *A61B 10/0096* (2013.01); *A61B 10/0283* (2013.01); *A61B 90/90* (2016.02);
(Continued)

(58) Field of Classification Search
CPC ....................................................... G01N 1/00
See application file for complete search history.

(56) References Cited

U.S. PATENT DOCUMENTS 5,526,822 A    6/1996 Burbank et al.
5,607,863 A *  3/1997 Chandler ............. B01L 3/5023
                                                     422/408
(Continued)

FOREIGN PATENT DOCUMENTS

JP    2008-128749 A     6/2008
WO    WO 2011/144982 A1  11/2001
(Continued)

OTHER PUBLICATIONS

Hahn, M., et al., "Vacuum-Assisted Breast Biopsy with Mammotome®,"Devicor Medical Germany GmbH, published in Germany by Springer Medizin Verlag, 2013, 130 pgs.

(Continued)

*Primary Examiner* — Jyoti Nagpaul
(74) *Attorney, Agent, or Firm* — Frost Brown Todd LLC

(57) ABSTRACT

An apparatus for individually storing multiple tissue samples separately from each other includes a base, a lid, a lock, and one or more vents. The base defines a plurality of reservoirs and a plurality of identification areas. A portion of the base defines an opening corresponding to each reservoir. The lid is configured to secure the multiple tissue samples within a corresponding reservoir by enclosing each corresponding opening in the closed configuration. The lock is configured to selectively lock the lid against the base in the closed configuration. The one or more vents are configured to enable entry of fluid into the reservoirs when the lid is in the closed configuration. The one or more vents are further configured to prevent exit of tissue samples from the reservoirs when the lid is in the closed configuration.

26 Claims, 20 Drawing Sheets

(51) Int. Cl.
*A61B 90/90* (2016.01)
*A61B 10/02* (2006.01)
*B01L 3/00* (2006.01)
*B01L 9/00* (2006.01)
*G01N 1/31* (2006.01)
*A61B 6/00* (2006.01)
*A61B 6/02* (2006.01)

(52) U.S. Cl.
CPC .......... *B01L 3/502* (2013.01); *B01L 3/50853* (2013.01); *B01L 9/523* (2013.01); *G01N 1/31* (2013.01); *A61B 6/022* (2013.01); *A61B 6/488* (2013.01); *A61B 6/502* (2013.01); *A61B 10/0041* (2013.01); *A61B 2010/0225* (2013.01); *B01L 9/52* (2013.01); *B01L 2200/025* (2013.01); *B01L 2200/0684* (2013.01); *B01L 2300/021* (2013.01); *B01L 2300/043* (2013.01); *B01L 2300/048* (2013.01); *G01N 2001/002* (2013.01); *G01N 2001/315* (2013.01)

(56) References Cited

U.S. PATENT DOCUMENTS

| | | |
|---|---|---|
| 5,928,164 A | 7/1999 | Burbank et al. |
| 6,017,316 A | 1/2000 | Ritchart et al. |
| 6,086,544 A | 7/2000 | Hibner et al. |
| 6,162,187 A | 12/2000 | Buzzard et al. |
| 6,432,065 B1 | 8/2002 | Burdorff et al. |
| 6,626,849 B2 | 9/2003 | Huitema et al. |
| 6,752,768 B2 | 6/2004 | Burdorff et al. |
| 7,442,171 B2 | 10/2008 | Stephens et al. |
| 7,648,466 B2 | 1/2010 | Stephens et al. |
| 7,715,523 B2 | 5/2010 | Lafferty |
| 7,837,632 B2 | 11/2010 | Stephens et al. |
| 7,854,706 B2 | 12/2010 | Hibner |
| 7,854,707 B2 | 12/2010 | Hibner et al. |
| 7,914,464 B2 | 3/2011 | Burdorff et al. |
| 7,938,786 B2 | 5/2011 | Ritchie et al. |
| 8,083,687 B2 | 12/2011 | Parihar |
| 8,118,755 B2 | 2/2012 | Hibner et al. |
| 8,177,728 B2 | 5/2012 | Hibner et al. |
| 8,206,316 B2 | 6/2012 | Hibner et al. |
| 8,235,913 B2 | 8/2012 | Hibner et al. |
| 8,241,226 B2 | 8/2012 | Hibner et al. |
| 8,251,916 B2 | 8/2012 | Speeg et al. |
| 8,454,531 B2 | 6/2013 | Speeg et al. |
| 8,485,987 B2 | 7/2013 | Videbaek et al. |
| 8,503,602 B2 | 8/2013 | Lafferty |
| 8,532,747 B2 | 9/2013 | Nock et al. |
| 8,628,482 B2 | 1/2014 | Leimbach et al. |
| 8,702,623 B2 | 4/2014 | Parihar et al. |
| 8,764,680 B2 | 7/2014 | Rhad et al. |
| 8,801,742 B2 | 8/2014 | Rhad et al. |
| 8,802,034 B2 | 8/2014 | Bartfeld et al. |
| 8,858,465 B2 | 10/2014 | Fiebig |
| 8,938,285 B2 | 1/2015 | Fiebig et al. |
| 8,951,207 B2 | 2/2015 | Hibner |
| 8,956,306 B2 | 2/2015 | Hibner |
| 9,056,317 B2 | 6/2015 | Bartfeld et al. |
| 9,095,326 B2 | 8/2015 | Ritchie et al. |
| 9,289,192 B2 | 3/2016 | Stone |
| 9,307,756 B2 | 4/2016 | Clement et al. |
| 9,326,755 B2 | 5/2016 | Fiebig et al. |
| 9,345,457 B2 | 5/2016 | Speeg et al. |
| 9,389,153 B2 | 7/2016 | Newby et al. |
| 9,409,164 B2 | 8/2016 | Tawfik et al. |
| 9,486,186 B2 | 11/2016 | Fiebig et al. |
| 9,724,076 B2 | 8/2017 | Fiebig et al. |
| 9,834,810 B2 | 12/2017 | Knapp, Jr. et al. |
| 9,877,706 B2 | 1/2018 | Speeg et al. |
| 9,955,955 B2 | 5/2018 | Fiebig et al. |
| 9,999,406 B2 | 6/2018 | Hibner et al. |
| 2006/0074345 A1 | 4/2006 | Hibner |
| 2009/0131821 A1 | 5/2009 | Speeg et al. |
| 2010/0152610 A1 | 6/2010 | Parihar et al. |
| 2010/0160819 A1 | 6/2010 | Parihar et al. |
| 2013/0324882 A1 | 12/2013 | Mescher |
| 2014/0039343 A1 | 2/2014 | Mescher et al. |
| 2015/0158027 A1 | 6/2015 | Fleming et al. |
| 2016/0183928 A1 | 6/2016 | Speeg et al. |
| 2018/0004918 A1 | 1/2018 | Walter et al. |

FOREIGN PATENT DOCUMENTS

| | | |
|---|---|---|
| WO | WO 2003/042788 A2 | 5/2003 |
| WO | WO 2007/014741 A2 | 2/2007 |
| WO | WO 2010/151761 A2 | 12/2010 |
| WO | WO 2013/192606 A1 | 12/2013 |
| WO | WO 2013/192607 A1 | 12/2013 |
| WO | WO 2014/151603 A1 | 9/2014 |
| WO | WO 2015/042107 A1 | 3/2015 |

OTHER PUBLICATIONS

Rolls, G., "101 Steps to Better Histology," Lecia Biosystems, 2016, Lecia Biosystems Melbourne Pty. Ltd., Melbourne, Australia, 140 pgs.

Rolls, G., "An Introduction to Tissue Processing," Lecia Biosystems, 2016, Lecia Biosystems Melbourne Pty. Ltd., Melbourne, Australia, 57 pgs.

Umfassende Histologielösungen (Total Histology Solutions), Leica Microsystems, Sep. 2010, 15 pgs.

International Search Report and Written Opinion dated Nov. 17, 2017 for Application No. PCT/US2017/040277, 12 pgs.

International Search Report and Written Opinion dated Jan. 9, 2018 for Application No. PCT/US2017/040273, 20 pgs.

U.S. Appl. No. 62/357,474, filed Jul. 1, 2016.

U.S. Appl. No. 62/406,480, filed Oct. 11, 2016.

Leica Microsystems, "Total Histology Solutions: Leica Microsystems' Complete Histology Product Range," Sep. 2010, 28 pgs.

\* cited by examiner

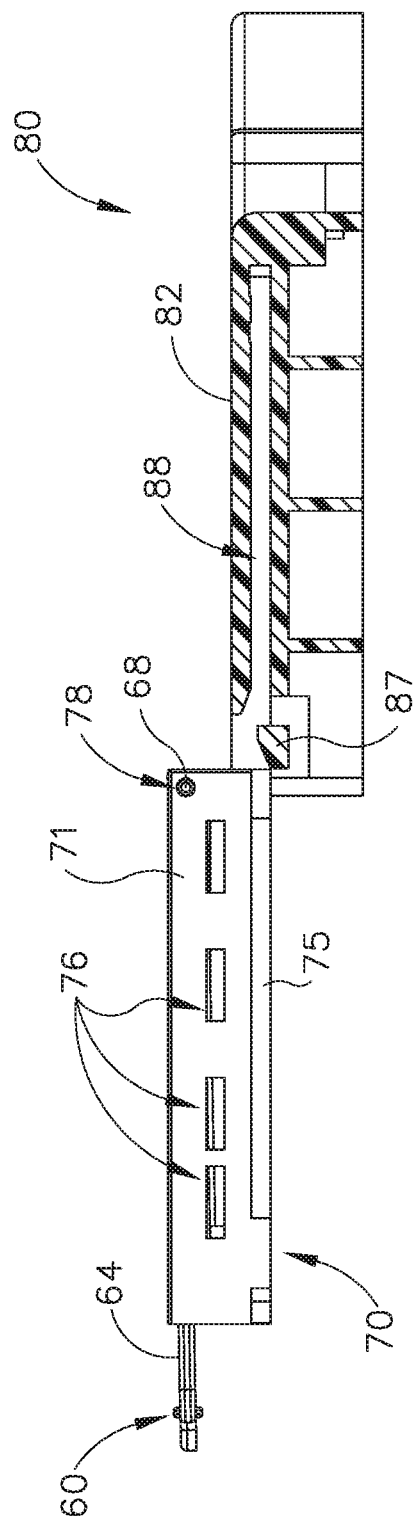

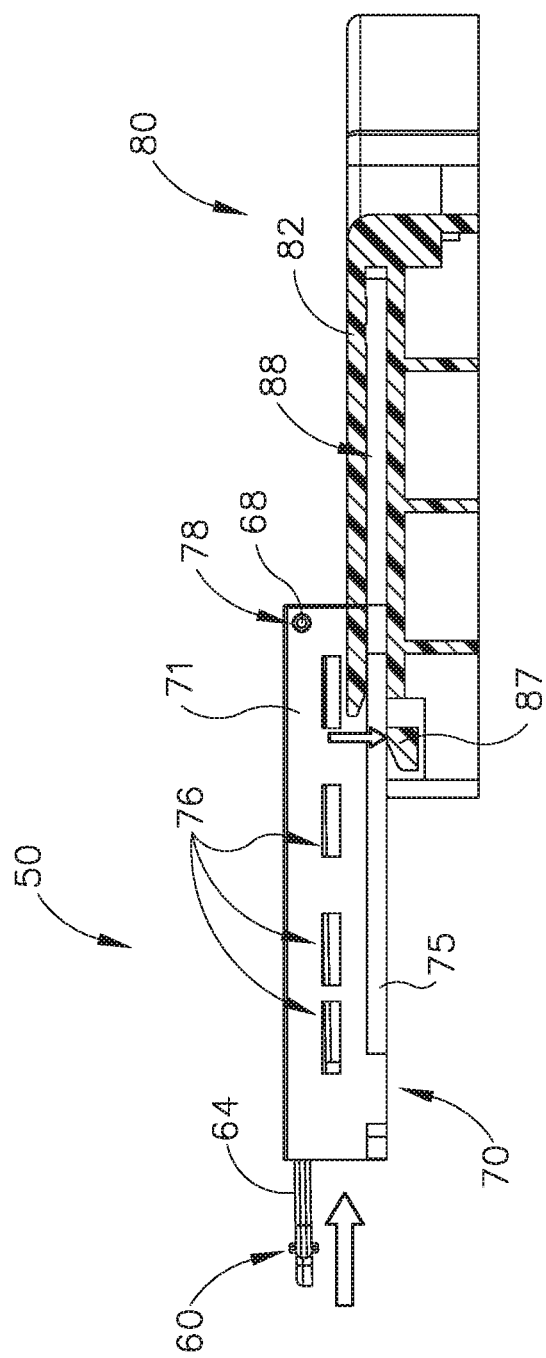

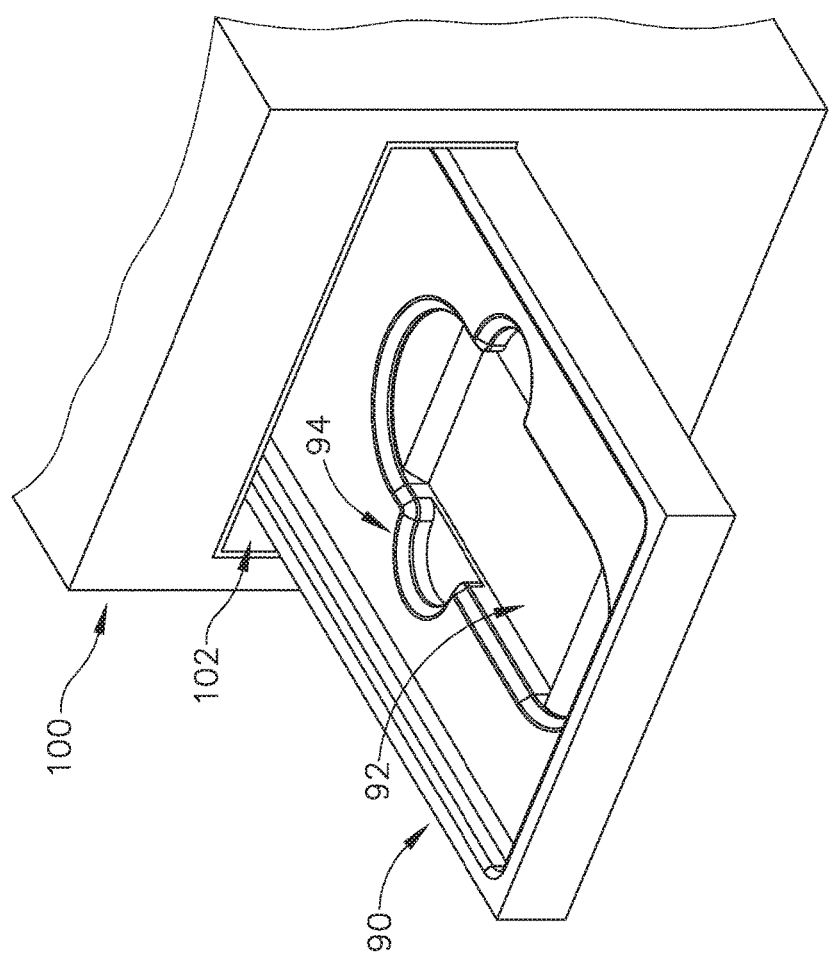

BIOPSY SAMPLE CONTAINER

PRIORITY

The present application claims priority to U.S. Provisional Patent Application No. 62/357,474, entitled "Biopsy Sample Container," filed on Jul. 1, 2016; and U.S. Provisional Patent Application No. 62/406,486, entitled "Biopsy Sample Container," filed on Oct. 11, 2016, the disclosures of which are hereby incorporated by reference herein in their entirety.

BACKGROUND

A biopsy is the removal of a tissue sample from a patient to enable examination of the tissue for signs of cancer or other disorders. Tissue samples may be obtained in a variety of ways using various medical procedures involving a variety of the sample collection devices. For example, biopsies may be open procedures (surgically removing tissue after creating an incision) or percutaneous procedures (e.g. by fine needle aspiration, core needle biopsy, or vacuum assisted biopsy). After the tissue sample is collected, the tissue sample may be analyzed at a lab (e.g. a pathology lab, biomedical lab, etc.) that is set up to perform the appropriate tests (such as histological analysis).

Biopsy samples have been obtained in a variety of ways in various medical procedures including open and percutaneous methods using a variety of devices. For instance, some biopsy devices may be fully operable by an operator using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

The state of the art for breast biopsy is vacuum-assisted breast biopsy. A current textbook in this area is "Vacuum-Assisted Breast Biopsy with Mammotome®" available Nov. 11, 2012, copyright 2013 by Devicor Medical Germany GmBh, published in Germany by Springer Medizin Verlag, Authors: Markus Hahn, Anne Tardivon and Jan Casselman, ISBN 978-3-642-34270-7.

Biopsy devices may be used under ultrasound image guidance, stereotactic (X-ray) guidance, MRI guidance, Positron Emission Mammography ("PEM" guidance), Breast-Specific Gamma Imaging ("BSGI") guidance, or otherwise. Each procedure has its own methodology based on the form of imaging guidance used. The following briefly describes ultrasound image guided biopsy procedures, stereotactic guided biopsy procedures and MRI guided biopsy procedures.

In an ultrasound image guided breast biopsy procedure, the operator may position an ultrasound transducer on the patient's breast and maneuver the transducer while viewing an ultrasound image display screen to locate suspicious tissue in the patient's breast. Once the operator locates the suspicious tissue, the operator may anesthetize the target region of the breast. Once the breast has been anesthetized, the operator may create an initial incision using a scalpel at a location on the exterior of the breast offset from the transducer. A needle of a breast biopsy probe disposed coaxially within an introducer cannula is then inserted into the breast through the initial incision. The operator continues to hold the ultrasound transducer with one hand while maneuvering the biopsy probe with the other hand. While viewing the ultrasound image on the display screen, the operator guides the needle to a position adjacent to the suspicious tissue. A cutter within the needle of the probe is used to remove tissue which is then conveyed either to a manual pick-up location on the breast biopsy device or to a tissue sample chamber. The needle of the breast biopsy device is then removed, leaving the introducer cannula disposed within the breast. The introducer cannula may then be used to introduce a biopsy marker cannula for deploying a biopsy site marker at the biopsy site. Once a marker has been deployed at the biopsy site, the biopsy marker cannula and the introducer cannula are both removed from the breast and the incision is closed using a medically acceptable way to close breaks in the skin.

In a stereotactic image guided breast biopsy procedure, the patient is first positioned relative to x-ray equipment, which includes a breast localization assembly. In some procedures, the patient is oriented in a prone position, with the patient lying face down on a procedure table with at least one breast hanging pendulously through an aperture in the procedure table. The breast is then compressed between a compression paddle and an x-ray receptor of a localization assembly that is positioned under the procedure table. A breast biopsy device is positioned on an automatic guide device in front of the compression paddle and between the breast and an x-ray source. Once positioning of the patient and localization of the breast are complete, a scout image is acquired with the x-ray receptor in a zero-degree angular position (i.e., the x-rays are emitted along an axis normal relative to the x-ray receptor). If the scout image indicates that the patient has been positioned in a desired position, the procedure may proceed with the acquisition of stereotactic image pairs. Stereotactic image pairs are acquired by orienting the x-ray source at various complementary angular positions relative to the x-ray receptor (e.g., +15° and)−15°), with at least one x-ray image acquired at each position.

Further in the stereotactic image guided breast biopsy procedure, once a suitable stereotactic image pair is acquired, an operator may identify a target site where biopsy sampling is desired by examining the stereotactic image pair. The target site is marked on each stereotactic image and a precise location of the target site on a Cartesian coordinate system is computed using an image processing module. The computed location of the target site is then communicated to the automatic guide device. The automatic guide device is responsive to this information to position the breast biopsy probe into a position that aligns with the target site. With the breast biopsy device positioned, an operator may then fire a needle of the biopsy probe into the breast of the patient, thereby positioning the needle at the target site. A cutter within the needle of the probe is used to remove tissue, which is then conveyed either to a manual pick-up location on the breast biopsy device or to a tissue sample chamber. After the biopsy tissue is removed, a biopsy marker cannula is inserted into the needle and is used to deploy a biopsy site marker at the biopsy site. Once a marker has been deployed at the biopsy site, the needle is removed from the breast and the incision is closed using a medically acceptable way to close breaks in the skin.

In an MRI guided breast biopsy procedure, after the patient is properly positioned on the table and a targeting device (e.g., a grid and cube combination or a pillar, post and cradle support combination) has been deployed and used, a baseline MRI image is taken to verify the target location. After that, a scalpel is used to incise the skin of the breast. Next, an assembly, formed by an obturator disposed in a sleeve, is inserted through the incision to penetrate the breast tissue under the skin. In some acceptable surgical techniques, the obturator is removed and an imaging rod is inserted into the sleeve in place of the obturator. An imaging rod is defined simply as an appropriately shaped rod that includes a feature that is detectable by an imaging technique being used for the biopsy procedure. The MRI image of the imaging rod is used to locate the site to which the sleeve/obturator assembly has penetrated. In some other acceptable surgical techniques, the obturator cooperates with the breast tissue to provide a visually observable artifact in an MRI image. With both of these techniques, after the location within the breast where the biopsy is to be taken is confirmed, the obturator or the imaging rod is removed.

Further in the MRI guided breast biopsy procedure, after the obturator or imaging rod has been removed, it is replaced in the sleeve with the needle of a breast biopsy probe. A cutter within the needle of the probe is used to remove tissue, which is then conveyed either to a manual pick up location on the breast biopsy device or to a breast biopsy device sample chamber. After the biopsy tissue is removed, a biopsy marker cannula is inserted into the needle and is used to deploy a biopsy site marker at the biopsy site. The needle is then removed from the sleeve. Optionally, the imaging rod or the obturator is put back into the breast for reimaging of the biopsy site. Then the imaging rod or obturator and the sleeve are removed.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "Mill Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; U.S. Pat. No. 8,118,755, entitled "Biopsy Sample Storage," issued Feb. 1, 2012; U.S. Pat. No. 8,206,316, entitled "Tetherless Biopsy Device with Reusable Portion," issued on Jun. 26, 2012; U.S. Pat. No. 8,241,226, entitled "Biopsy Device with Rotatable Tissue Sample Holder," issued on Aug. 14, 2012; U.S. Pat. No. 8,251,916, entitled "Revolving Tissue Sample Holder for Biopsy Device," issued Aug. 28, 2012; U.S. Pat. No. 8,454, 531, entitled "Icon-Based User Interface on Biopsy System Control Module," published May 21, 2009, issued on Jun. 4, 2013; U.S. Pat. No. 8,532,747, entitled "Biopsy Marker Delivery Device," issued Sep. 10, 2013; U.S. Pat. No. 8,702,623, entitled "Biopsy Device with Discrete Tissue Chambers," issued on Apr. 22, 2014; U.S. Pat. No. 8,764,680, entitled "Handheld Biopsy Device with Needle Firing," issued on Jun. 11, 2014; U.S. Pat. No. 8,801,742, entitled "Needle Assembly and Blade Assembly for Biopsy Device," issued Aug. 12, 2014; U.S. Pat. No. 8,858,465, entitled "Biopsy Device with Motorized Needle Firing," issued Oct. 14, 2014; U.S. Pat. No. 8,938,285, entitled "Access Chamber and Markers for Biopsy Device," issued Jan. 20, 2015; U.S. Pat. No. 9,095,326, entitled "Biopsy System with Vacuum Control Module," issued Aug. 4, 2015; U.S. Pat. No. 9,095,326, entitled "Biopsy System with Vacuum Control Module," issued Aug. 4, 2015 and U.S. Pat. No. 9,326,755, entitled "Biopsy Device Tissue Sample Holder with Bulk Chamber and Pathology Chamber," issued May 3, 2016. The disclosure of each of the above-cited U.S. Patents is incorporated by reference herein.

Additional exemplary biopsy devices and biopsy system components are disclosed in U.S. Pub. No. 2006/0074345, entitled "Biopsy Apparatus and Method," published Apr. 6, 2006 and now abandoned; U.S. Pub. No. 2008/0214955, entitled "Presentation of Biopsy Sample by Biopsy Device," published Sep. 4, 2008; U.S. Pub. No. 2009/0131821, entitled "Graphical User Interface For Biopsy System Control Module," published May 21, 2009, now abandoned; U.S. Pub. No. 2010/0152610, entitled "Hand Actuated Tetherless Biopsy Device with Pistol Grip," published Jun. 17, 2010, now abandoned; U.S. Pub. No. 2010/0160819, entitled "Biopsy Device with Central Thumbwheel," published Jun. 24, 2010, now abandoned; U.S. Pub. No. 2013/0144188, entitled "Biopsy Device With Slide-In Probe," published Jun. 6, 2013; and U.S. Pub. No. 2013/0324882, entitled "Control for Biopsy Device," published Dec. 5, 2013. The disclosure of each of the above-cited U.S. Patent Application Publications is incorporated by reference herein.

U.S. Pub. No. 2014/0275999, entitled "Biopsy device" published Sep. 18, 2014, and U.S. Pub. No. 2016/0183928, entitled "Biopsy Device," published Jun. 30, 2016, both describe some aspect of a biopsy device including a probe, a holster, and a tissue sample holder for collecting tissue samples. The probe includes a needle and a hollow cutter. The tissue sample holder includes a housing having a plurality of chambers that are configured to receive a plurality of strips connected by at least one flexible member. The flexible member is configured to permit the strips to pivot relative to each other such that the strips can shift between a flat configuration and an arcuate configuration. The tissue sample holder is rotatable to successively index each chamber to the cutter lumen such that tissue samples may be collected in the strips. The strips may be removed from the tissue sample holder and placed in a tissue sample holder container for imaging of tissue samples.

Leica Biosystems is a global leader in workflow solutions and automation, providing anatomic pathology labs and researchers a comprehensive product range for each step in the pathology process from sample preparation and staining to imaging and reporting. Leica Biosystems has published on their website informational booklets that are accessible via download and that contain information on various aspects of the pathology process. These booklets include, but are not limited to: "An Introduction to Tissue Processing" by Geoffrey Rolls, "101 Steps to Better Histology," and "Total Histology Solutions," all of which are available via www.leicabiosystems.com.

At several steps during tissue processing using conventional techniques and instruments, it may be necessary to manually manipulate the tissue. This manual manipulation may take time and introduce the possibility of human error causing mistakes during the processing of tissue. Any and all mistakes during the processing of tissue may make the pathological examination of the tissue much more problematic to achieve the desired goal of having an accurate diagnosis. Thus, it is understood that a desired goal of modern tissue processing is the reduction of the requirement that tissue be manually manipulated.

International Pat. Pub. No. WO 2013/192606, entitled "Biopsy Tissue Sample Transport Device and Method of Using Thereof," published on Dec. 27, 2013, describes a biopsy tissue sample transport device and method of using the same including a tissue storage assembly having a sample container, having a holding structure to hold a tissue sample, the holding structure having a sample access opening formed in a sidewall; a housing that receives the tissue storage assembly, the housing comprising an assembly insertion opening through which the tissue storage assembly is inserted into the housing; a sealing member configured to engage and substantially seal the sample access opening of the holding structure of the sample container of the tissue storage assembly; and a lid to engage and substantially seal the assembly insertion opening of the housing.

International Pat. Pub. No. WO 2013/192607, entitled "Tissue Sample Container and Methods," published on Dec. 27, 2013, describes a tissue sample container including a base having a plurality of sample holding sections, which are configured to receive a plurality of tissue samples in a given orientation and are demarcated by section walls; and a lid configured to sealingly engage the base. The sample holding sections are sized and shaped to correspond to a specific tissue sample size and shape such that the base in cooperation with the section walls, maintain the given orientation and identity of the tissue samples within respective sample holding sections.

International Pat. Pub. No. WO 2014/151603, entitled "Biopsy Device," published on Sep. 25, 2014, describes a biopsy device that includes a probe, a holster, and a tissue sample holder for collecting tissue samples. The probe includes a needle and a hollow cutter. The tissue sample holder includes a housing having a plurality of chambers that are configured to receive a plurality of strips connected by at least one flexible member. The flexible member is configured to permit the strips to pivot relative to each other such that the strips can shift between a flat configuration and an arcuate configuration. The tissue sample holder is rotatable to successively index each chamber to the cutter lumen such that tissue samples may be collected in the strips. The strips may be removed from the tissue sample holder and placed in a tissue sample holder container for imaging of tissue samples.

U.S. Pat. No. 7,715,523, entitled "System and Apparatus for Rapid Stereotactic Breast Biopsy Analysis," issued on May 11, 2010, and U.S. Pat. No. 8,503,602, entitled "System and Apparatus for Rapid Stereotactic Breast Biopsy Analysis," issued on Aug. 6, 2013, both describe a stereotactic breast biopsy apparatus and system that may comprise an x-ray source, a digital imaging receptor, and a biopsy specimen cassette, wherein the x-ray source is provided with a means for displacing the beam axis of the x-ray source from a working biopsy corridor beam axis to permit an unobstructed illumination of the biopsy specimen and thereby produce biopsy x-ray images directly in the procedure room for immediate analysis. Some examples of the benefits may be, but are not limited to, a more rapid analysis of biopsy specimen digital images, post-processing image capability, and decreased procedure time and diminution of patient bleeding complications and needle discomfort.

U.S. Pat. No. 8,485,987, entitled "Tissue Handling System with Reduced Operator Exposure," issued Jul. 16, 2016, describes a tissue handling system includes a biopsy device having an invasive unit with tissue-receiving and tissue-severing components being capable of harvesting and bringing at least one tissue sample to a point outside the body of a patient. The tissue handling system further includes a tissue collecting device adapted to be brought in detachable operative engagement with the tissue-receiving components of the biopsy device to remove the at least one tissue sample. Additionally, the tissue handling device comprises a tissue storage container configured to receive the at least one tissue sample, the entire tissue collecting device, or the part of the collecting device that contains the at least one tissue sample. The tissue storage container further is configured to receive a volume of preserving agent. The tissue handling system also comprises a vessel including the preserving agent adapted to be gas-tightly mated or coupled to the tissue storage container.

U.S. Pat. No. 8,802,034, entitled "Tissue Container for Molecular and Histology Diagnostics Incorporating a Breakable Membrane," issued on Aug. 12, 2014, describes a container for storing a biological sample for molecular diagnostic testing and/or histological testing. The container includes a first chamber for receiving a sample holder therein, a second chamber, and a closure for enclosing the container. A breakable membrane, such as a pierce-able foil, extends within the container and separates the two chambers. When the breakable membrane is broken, fluid can pass between the first and second chambers. The membrane may be broken through an activator on the closure, such as a depressible member or a rotatable carrier, causing the sample holder to break through the membrane.

U.S. Pat. No. 9,056,317, entitled "Tissue Container for Molecular and Histology Diagnostics Incorporating a Breakable Membrane," issued on Jun. 16, 2016 describes a container for storing a biological sample for molecular diagnostic testing and/or histological testing. The container includes a first chamber for receiving a sample holder therein, a second chamber, and a closure for enclosing the container. A breakable membrane, such as a pierce able foil, extends within the container and separates the two chambers. When the breakable membrane is broken, fluid can pass between the first and second chambers. The membrane may be broken through an activator on the closure, such as a depressible member or a rotatable carrier, causing the sample holder to break through the membrane.

While several systems and methods have been made and used for obtaining and processing a biopsy sample, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIG. 8A depicts a side cross-sectional view, taken along line 8-8 of FIG. 7, of the tissue container of FIG. 3 aligned to be coupled with the adaptor of FIG. 6;

FIG. 8B depicts a side cross-sectional view, taken along line 8-8 of FIG. 7, of the tissue container of FIG. 3 being coupled with the adaptor of FIG. 6;

FIG. 11A depicts a perspective view of the radiograph drawer of FIG. 9 in an open configuration relative to a radiograph machine;

Figure 1:
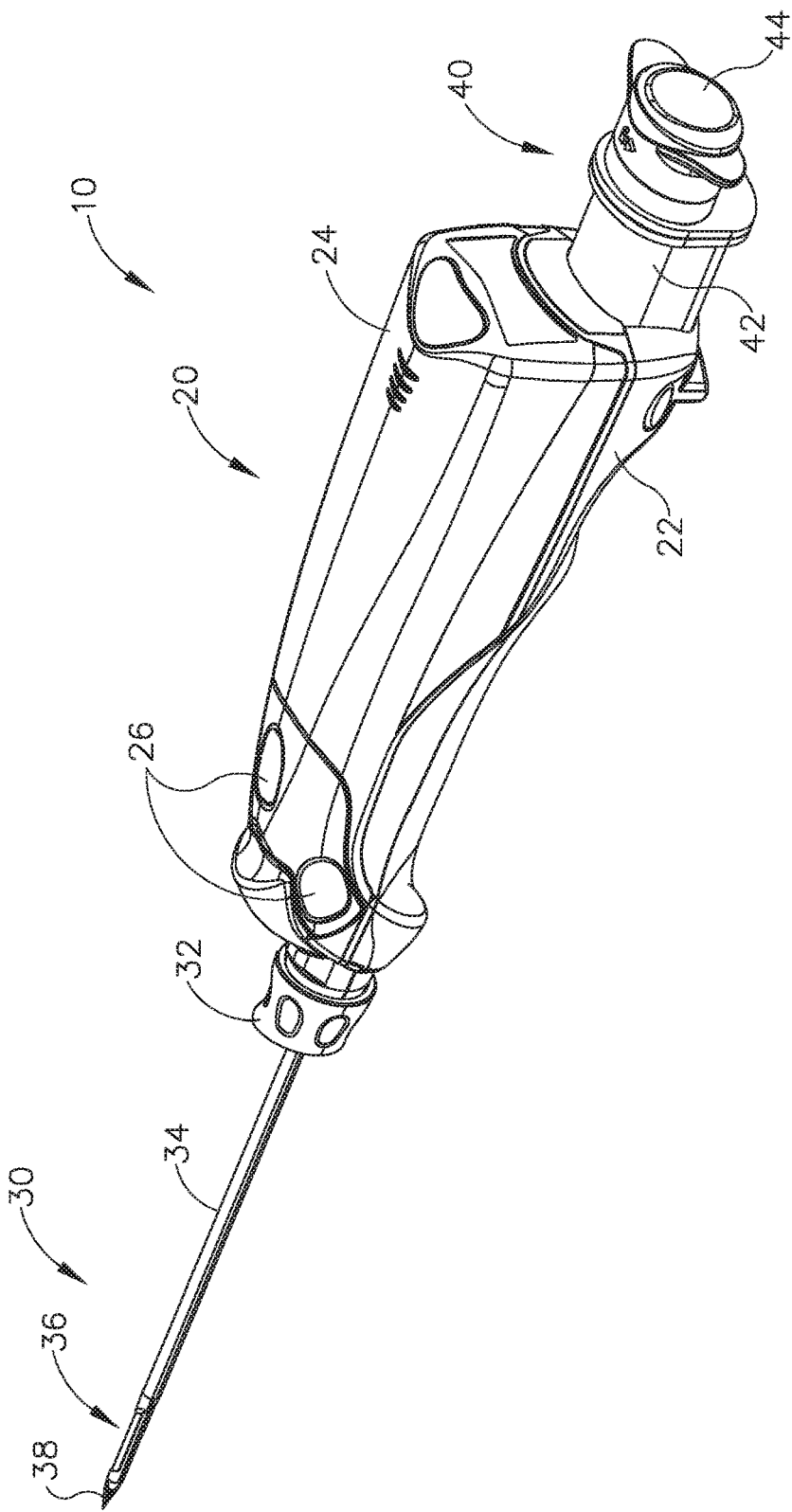
FIG. 1 depicts a perspective view of an exemplary biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Biopsy devices may be used to collect tissue samples in a variety of ways. For example, in some instances tissue samples are collected into a single tissue basket such that all tissue samples collected during a given biopsy procedure are deposited into a single tissue sample basket. In such instances, challenges may be encountered when transporting tissue samples through various diagnostic steps after the tissue samples have been collected. For example, in some procedures where tissue samples are collected in a single sample basket, such tissue samples may be preliminarily laid out on gauze or a tray. Specimen radiograph can then be performed in either the procedure room or at a remote location. Tissue samples may additionally be grouped and/or dyed at this stage. Once preliminary analysis has been completed, the tissue samples are loaded into a formalin jar and then transported to a remote pathology lab.

One consequence of the procedure described above is that tracking of individual tissue samples may be challenging. However, it may nonetheless be desirable to track individual tissue samples throughout the biopsy sampling and subsequent diagnostic procedures. In some instances, such tracking may be desirable to enhance the ability to obtain specific analysis of tissue samples identified by the operator collecting biopsy samples. In addition, or in the alternative, such tracking may be desirable to avoid or otherwise prevent operator error during the entire biopsy sample collection and analysis process. Various devices are described herein that may be used to enhance the tracking of tissue samples as they progress through the biopsy sample collection and analysis process. Although numerous features and configures are described herein, it should be understood that various modifications may be made as will be apparent to those of ordinary skill in the art in view of the teachings herein.

I. Exemplary Biopsy Device

FIG. 1 depicts an exemplary biopsy device (10) that can be used to acquire tissue samples from a patient. Biopsy device (10) comprises a body (20), a needle assembly (30), and a tissue sample holder (40). Body (20) is generally configured for grasping by an operator using a single hand. In the present example, biopsy device (10) is configured for tetherless biopsy procedures. Accordingly, body (20) confines all of the components necessary for operation of biopsy device (10) such as motors, vacuum pumps, drive mechanisms, electronics, etc. into a single handheld unit.

The internal components of biopsy device (10) may be configured and operable in accordance with at least some of the teachings of U.S. Pat. No. 7,854,706, entitled "Clutch and Valving System for Tetherless Biopsy Device," issued on Dec. 21, 2010; U.S. Pat. No. 7,938,786, entitled "Vacuum Timing Algorithm for Biopsy Device," issued on May 10, 2011; U.S. Pat. No. 8,038,627, entitled "Biopsy Device with Translating Valve Mechanism," issued on Oct. 18, 2011; U.S. Pat. No. 8,177,728, entitled "Valve Mechanism for Tetherless Biopsy Device," issued on May 15, 2012; U.S. Pat. No. 8,235,913, entitled "Biopsy Device with Translating Valve Member," issued on Aug. 7, 2012; U.S. Pat. No. 8,951,207, entitled "Tetherless Biopsy Device," issued on Feb. 10, 2015; and/or U.S. Pat. No. 8,956,306, entitled "Biopsy Device with Integral Vacuum Assist and Tissue Sample and Fluid Capturing Canister," issued on Feb. 17, 2015, the disclosures of which are incorporated by reference herein.

Body (20) of the present example comprises a probe (22) and a holster (24). Probe (22) and holster (24) are removably attachable to each other. Holster (24) of the present example comprises a plurality of operator input features (26). Operator input features (26) are positioned for actuation with a single hand of an operator. When one or more of user operator features (26) are actuated by an operator, a sampling sequence is initiated. This permits an operator to selectively acquire a biopsy sample using needle assembly (30). The acquired biopsy sample is then transported though probe (22) to tissue sample holder (40).

Needle assembly (30) extends distally from probe (22). In the present example, needle assembly (30) includes a rotation knob (32) an outer cannula (34), a lateral aperture (36), and a sharp distal tip (38). Rotation knob (32) of the present example is configured to permit an operator to selectively rotate needle assembly (30) relative to a longitudinal axis defined by needle assembly (30). By way of example only, rotation knob (32) may be configured and operable in accordance with at least some of the teachings of U.S. Pat. No. 8,764,680, entitled "Handheld Biopsy Device with Needle Firing," issued on Jul. 1, 2014, the disclosure of which is incorporated by reference herein.

Outer cannula (34) extends distally from rotation knob (32). Outer cannula (34) of the present example comprises a generally oval-shaped lateral cross-section. In other examples, outer cannula (34) may include any other suitable cross-sectional shape as will be apparent to those of ordinary skill in the art in view of the teachings herein. Although not shown, it should be understood that outer cannula (34) encloses a hollow cylindrical cutter. The cutter is rotatable and translatable within outer cannula (34) to sever a tissue sample disposed within lateral aperture (36).

Sharp distal tip (38) is disposed on the distal end of outer cannula (34). In the present example, sharp distal tip (38) is used to pierce and penetrate tissue. Lateral aperture (36) is positioned just proximally of sharp tip (38). Accordingly, it should be understood that sharp tip (38) permits an operator to position lateral aperture (36) within a patient at a particular region of interest for biopsy sample acquisition. By way of example only, distal tip (38) may be configured and operable in accordance with at least some of the teachings of U.S. Pat. No. 8,628,482, entitled "Needle Tip for Biopsy Device," issued on Jan. 14, 2014, the disclosure of which is incorporated by reference herein.

Figure 2:
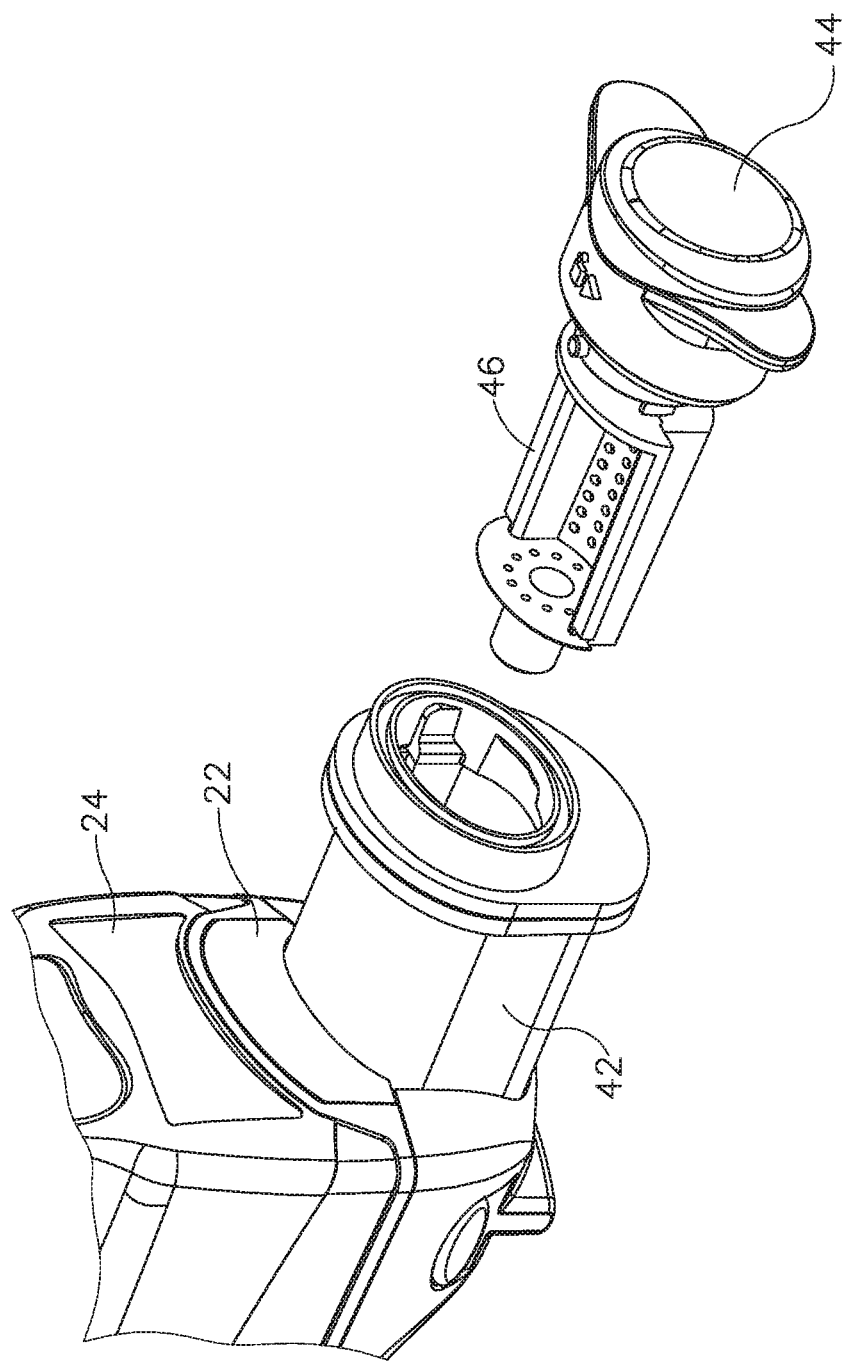
FIG. 2 depicts a partially exploded perspective view of a tissue sample holder of the biopsy device of FIG. 1.

Tissue sample holder (40) extends proximally from probe (22). Tissue sample holder (40) comprises an outer cup (42), a cap (44), and a tissue basket (46). As can be best seen in FIG. 2, tissue basket (46) is removably receivable within outer cup (42). In particular, tissue basket (46) extends distally from cap (44), which is used to insert tissue basket (46) into outer cup (42). Once inserted therein, cap (44) may be selectively locked to outer cup (42) to seal outer cup (42) and lock cap (44) to outer cup (42). By way of example only, tissue sample holder (40) may be configured and operable in accordance with at least some of the teachings of U.S. Pat. Pub. No. 2012/0065542, entitled "Biopsy Device Tissue Sample Holder with Removable Tray," published on Mar. 15, 2012, the disclosure of which is incorporated by reference herein.

Tissue basket (46) of the present example is a basket-style tissue container. It should be understood that in this context the term "basket-style" refers to a container that is configured to store tissue samples in a bulk configuration with each acquired tissue sample intermixed with all other tissue samples. Thus, tissue basket (46) does not discretely separate tissue samples from each other within tissue sample holder (40). Accordingly, should an operator wish to separate certain tissue samples from others, such an operation is performed by manually separating each tissue sample in accordance with a desired arrangement, using forceps or some other kind of instrumentation to grasp and sort the tissue samples.

Although the various features and concepts described herein are described in connection with a tetherless version of biopsy device (10), it should be understood that no such limitation is intended. For instance, in other examples a tethered biopsy device may be used in lieu of biopsy device (10). By way of example only, such tethered biopsy devices can be in communication with a control module, which may communicate fluids and/or electrical signals to and from such biopsy device. Such tethered biopsy devices may be configured and operable in accordance with at least some of the teachings of U.S. Pub. No. 2014/0039343, entitled "Biopsy System," published Feb. 6, 2014, the disclosure of which is incorporated by reference herein. Other alternative biopsy devices will be apparent to those of ordinary skill in the art in view of the teachings herein. It should therefore be understood that the following teachings are not necessarily dependent upon the particular kind of biopsy device that is used to obtain the tissue samples.

II Exemplary Tissue Container

Figure 3:
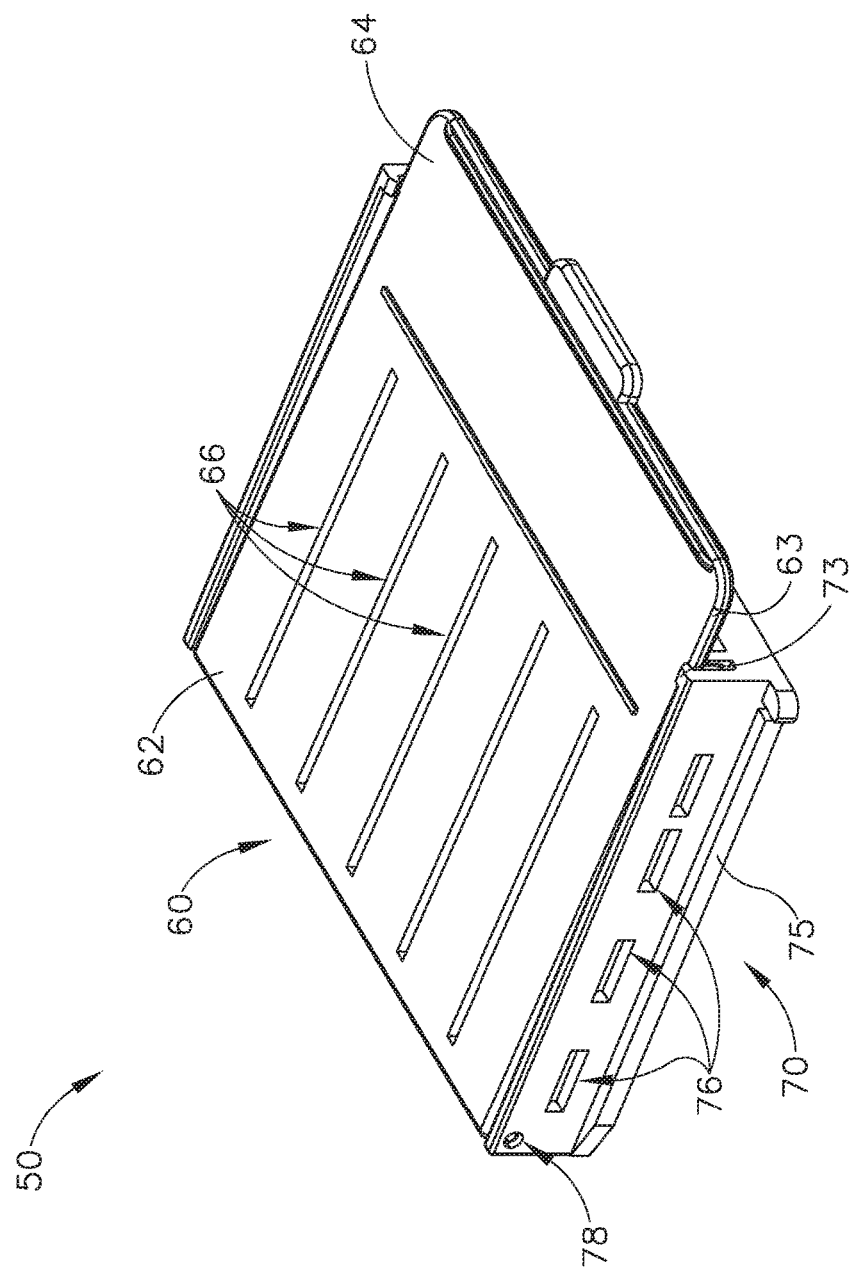
FIG. 3 depicts a perspective view of an exemplary tissue container in a closed configuration.
Figure 4:
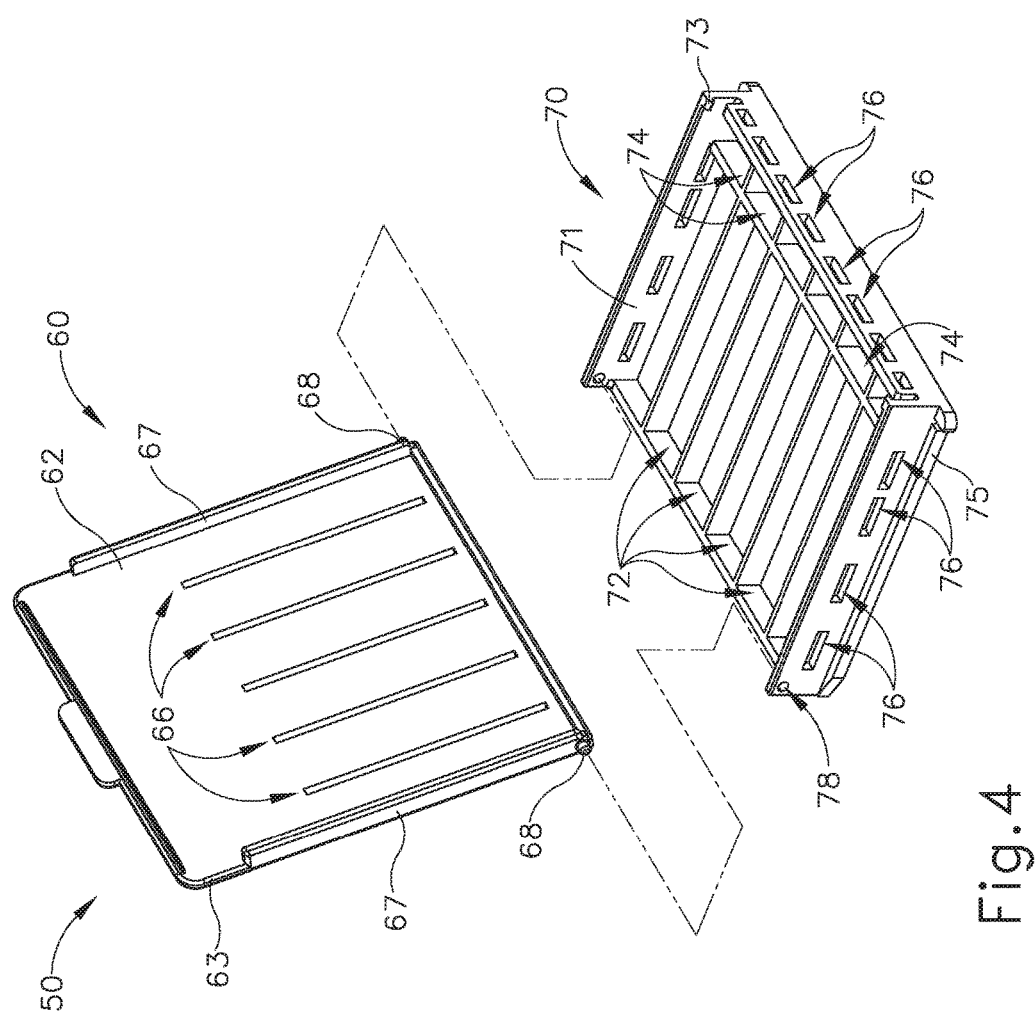
FIG. 4 depicts an exploded perspective view of the tissue container of FIG. 3.
Figure 5:
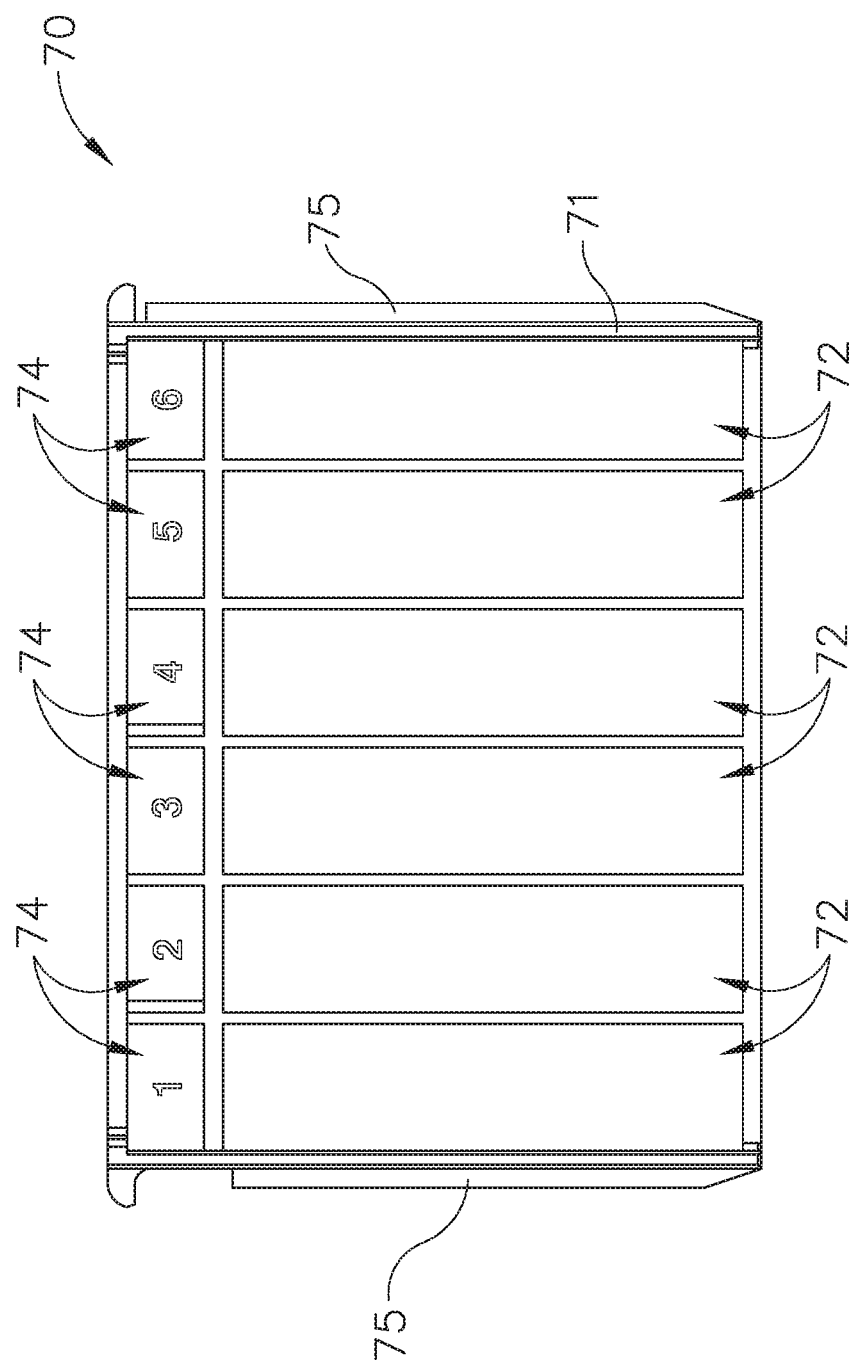
FIG. 5 depicts a top plan view of a container base of the tissue container of FIG. 3.

FIGS. 3-5 show an exemplary tissue container (50) that may be used to store tissue samples taken with biopsy device (10). As will be described in greater detail below, tissue container (50) may accept single tissue samples that an operator picks from the tissue basket (46) and places into separated reservoirs for separate identification.

Tissue container (50) includes a lid (60) pivotally coupled to a base (70). Lid (60) includes lid body (62) defining a plurality of longitudinal vents (66), a label area (64) unitarily extending from lid body (62), rounded edges (63), a pair of side rails (67), and a pair of pivot studs (68). Base (70) includes a base body (71) defining a plurality of rectangular shaped reservoirs (72), a corresponding identification area (74) for each reservoir (72), a plurality of peripheral vents (76), and a pair of pivot holes (78). Base (70) also includes a pair of resilient tabs (73) and a pair of guide rails (75).

As will be described in greater detail below, lid (60) is capable of pivoting relative to base (70) from an open configuration (FIG. 10) to a closed configuration (FIG. 3) in order to store multiple tissue samples individually separated from each other. Additionally, tissue samples may be individually stored throughout the imaging process and the transport process without direct tissue handling in between. While lid (60) pivots between open and closed positions in the present example, it should be understood that, in other variations, lid (60) may slide or otherwise move between open and closed positions. Thus, pivotal movement of lid (60) is not required.

Lid (60) may be made out of a material that is transparent. Therefore, an operator may see though lid (60) in order to examine the contents stored within tissue container (50) as well as any information displayed on base (70), while lid (60) is in a closed position. Lid (60) also has a label area (64), providing sufficient space to adequately label tissue container (50) with any desired information. In the current example, label area (64) extends past base (70) while lid (60) is in the closed configuration shown in FIG. 3, though it should be understood that this is merely optional.

Pivot studs (68) of lid (60) are configured to be received within pivot holes (78) defined by base body (71) of base (70). Pivot studs (68) and pivot holes (78) allow lid (60) to pivot relative to base (70). While in the current example, pivot studs (68) and pivot holes (78) are used to pivotally couple lid (60) with base (70), any other suitable means of pivotally coupling lid (60) and base (70) may be used as would be apparent to one having ordinary skill in the art in view of the teachings herein. For instance, a living hinge may pivotally couple lid (60) and base (70). Additionally, while in the current example, lid (60) and base (70) are pivotally coupled to each other, this is merely optional. For instance, lid (60) may instead be slideably coupled to base (70) such that lid (60) slides within slots defined by base (70). Alternatively, or additionally, lid (60) may be able to selectively couple with base (70), such that lid (60) snaps into place when an operator forces lid (60) onto base (70). Alternatively, any other suitable means of coupling base (70) and lid (60) may be used as would be apparent to one having ordinary skill in the art in view of the teachings herein.

Resilient tabs (73) of base (70) are designed to deflect outwardly from a natural position to a deflected position in repose to contact with rounded edges (63) of lid (60) when lid (60) pivots toward base (70). Once lid (60) pivots to a configuration where rounded edges (63) are under resilient tabs (73), resilient tabs (73) resiliently return to their natural position. When lid (60) is under resilient tabs (73), lid (60) is effectively locked into place. In other words, when lid (60) pivots to a closed configuration against base (70), resilient tabs (73) will prevent lid (60) from inadvertently pivoting from the closed configuration to a more open configuration.

It should be understood an operator may forcefully pivot lid (60) from the closed configuration above resilient tabs (73) in order to snap open lid (60) relative to resilient tabs (73), thereby effectively unlocking lid (60) relative to base (70). While the current example uses resilient tabs (73) in order to lock lid (60) in the closed configuration, it should be understood any other suitable locking mechanism may be used in order to selectively lock lid (60) in the closed configuration as would be apparent to one having ordinary skill in the art in view of the teachings herein. By way of example only, snaps and recesses may be used as an alternative.

As best seen in FIGS. 4-5, reservoirs (72) are capable of discretely storing individual tissue samples such that each tissue sample is prevented from leaving one reservoir (72) for another reservoir (72) once lid (60) is pivoted closed. In the current example, there are six individual reservoirs (72). However, any suitable number of reservoirs (72) may be provided as would be apparent to one having ordinary skill in the art in view of the teachings herein.

The portion of base body (71) defining reservoir (72) encloses a complete perimeter of reservoir (72). Therefore, all that is required in order to store individual tissue samples for individual identification is to place the desired tissue samples in corresponding reservoirs (72) while lid (60) is in the open configuration, and then move lid (60) to the closed position. In other words, no additional equipment is needed in order to individually store tissue samples separately from each other. In the present example, the enclosed perimeter is rectangular. However, any other suitable perimeter geometry may be utilized as would be apparent to one having ordinary skill in the art in view of the teachings herein. For example, the enclosed perimeter of reservoir (72) may be triangular, elliptical, or of any other suitable configuration.

Each individual reservoir (72) includes a corresponding identification area (74). Identification areas (74) are directly adjacent to respective reservoirs (72). As best seen in FIG. 5, identification areas (74) utilize numbers to identify respective reservoirs (72). However, any other suitable identification features may be utilized as would be apparent to one having ordinary skill in the art in view of the teachings herein, such as letters, etc. In the current example, identification areas (74) are separated from respective individual reservoirs (72). However, this is merely optional, as identification areas (74) may instead be placed in a location that coincides with respective individual reservoirs (72).

During the transportation process, it may be desirable to immerse tissue samples in a preserving fluid, such as formalin, in order to maintain the integrity of tissue samples. Vents (66, 76) may help provide fluid communication between reservoirs (72) and the exterior of tissue container (50). Therefore, if tissue container (50), in the closed configuration, is immersed in a fluid, such as formalin, vents (66, 76) may help ensure that reservoirs (72) also fill with fluid.

Of course, vents (66, 76) are merely optional. For instance, lid (60) and base (70) may be designed to define a gap when lid (60) is in the closed position as shown in FIG. 3. The gap may be small enough to prevent tissue samples from escaping reservoirs (72), but large enough to allow sufficient fluid communication between reservoirs (72) and the exterior of tissue container (50) such that reservoirs (72) may fill with a fluid when tissue container (50) is submerged within the fluid. Other suitable features that may be provided to enable entry of fluid into reservoirs (72) when lid (60) is closed, while preventing tissue samples from escaping reservoirs (72), will be apparent to those of ordinary skill in the art in view of the teachings herein.

As mentioned above, lid (60) also has two side rails (67). Side rails (67) are dimensioned to overlap with the outer perimeter of the outermost reservoirs (72). Therefore, side rails (67) may help ensure that there is no gap between the outer perimeter of the outermost reservoirs (72) and lid (60) while lid (60) is in the closed position. Side rails (67) may help prevent tissue samples located within the outermost reservoirs (72) from escaping tissue container (50) when lid (60) is in the closed position.

As also mentioned above, base (70) also includes a pair of guide rails (75). As will be described in greater detail below, guide rails (75) may be utilized to couple tissue container (50) with an adaptor (80) such that tissue container (50) is effectively fixed relative to adaptor (80).

In addition to, or in lieu of, the foregoing, at least a portion of tissue container (50) may be constructed and operable in accordance with at least some of the teachings of U.S. Pub. No. 2014/0275999, entitled "Biopsy Device," published Sep. 18, 2014, the disclosure of which is incorporated by reference herein. Various suitable ways in which the teachings herein may be combined with the teachings of U.S. Pub. No. 2014/0275999 will be apparent to those of ordinary skill in the art

III. Exemplary Adaptor

Figure 6:
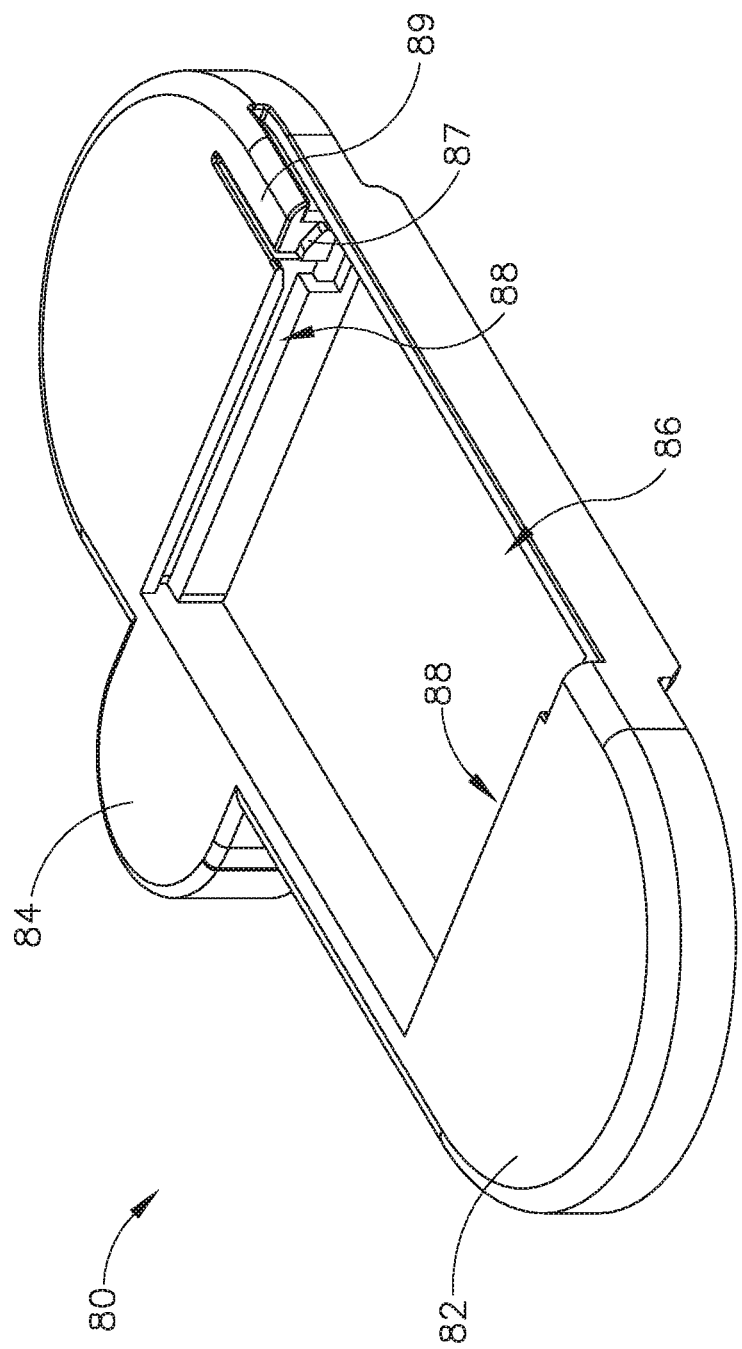
FIG. 6 depicts a perspective view of an exemplary adaptor that may be used to receive the tissue container of FIG. 3.
Figure 7:
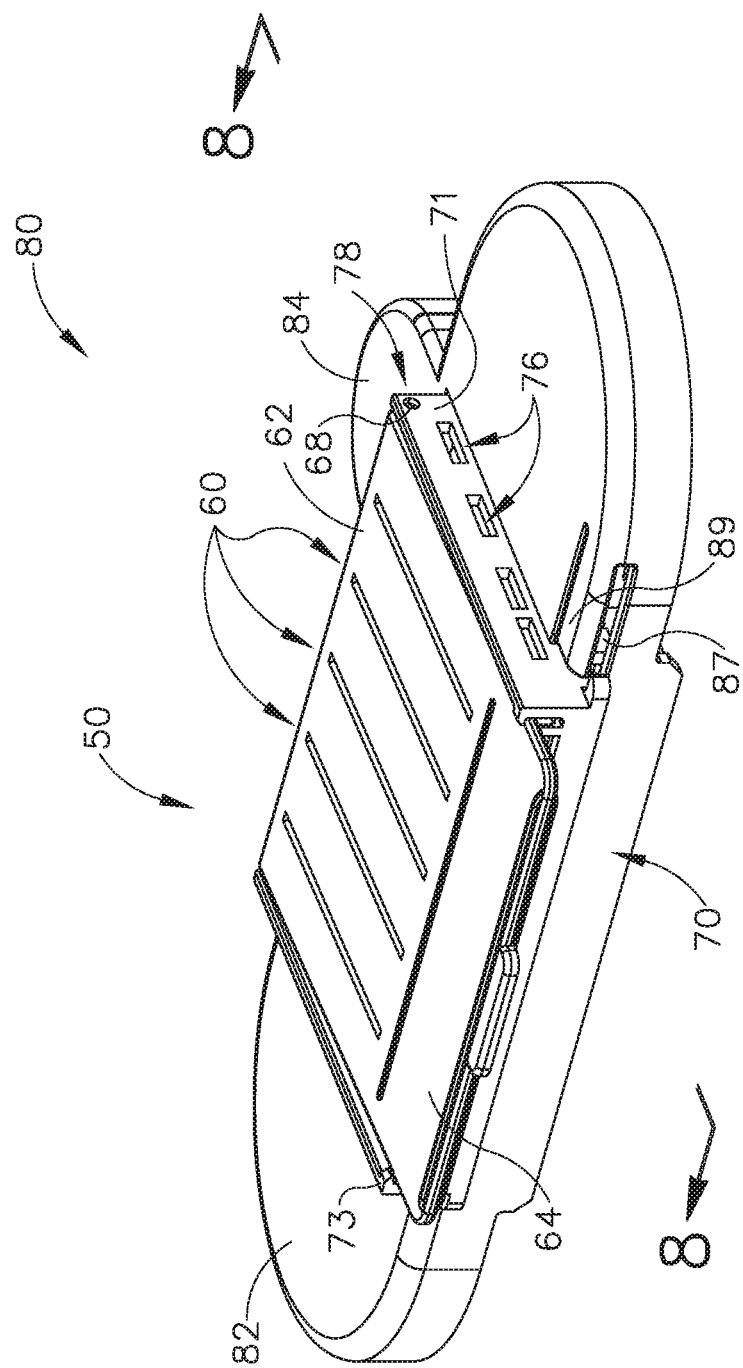
FIG. 7 depicts a perspective view of the tissue container of FIG. 3 coupled with the adaptor of FIG. 6.

FIG. 6 shows an exemplary adaptor (80) that may be utilized to couple with tissue container (50) described above. As will be described in greater detail below, adaptor (80) may be used to insert tissue container (50) within a drawer (90) of a radiograph machine (100), such that tissue container (50) is placed in a consistent location relative to drawer (90). Consistent placement of tissue container (50) relative to drawer (90) may help ensure accurate analysis of tissue samples by radiograph machine (100).

Figure 8C:
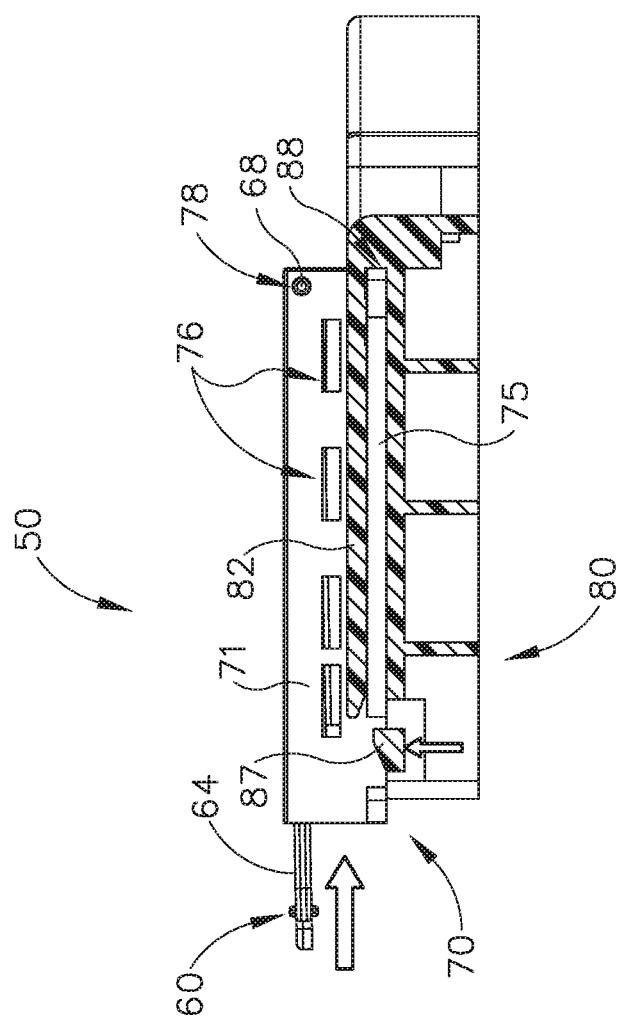
FIG. 8C depicts a side cross-sectional view, taken along line 8-8 of FIG. 7, of the tissue container of FIG. 3 coupled with the adaptor of FIG. 6.

Adaptor (80) includes an adaptor body (82) defining a container recess (86) and a pair of opposed guide slots (88), a locating feature (84), a resilient arm (89), and a stop (87) fixed to resilient arm (89). Container recess (86) is dimensioned to house tissue container (50). Container recess (86) may complement the underside of tissue container (50). Guide slots (88) are dimensioned to receive guide rails (75) of tissue container (50). Resilient arm (89) is sufficiently resilient to deflect downwardly toward container recess (86) in response to an external force. As best seen between FIGS. 8A-8B, stop (87) is dimensioned to abut against guide rail (75) as they slide within guide slots (88), thereby deflecting resilient arm (89) and stop (87) downwardly toward container recess (86). As best seen in FIG. 8C, once tissue container (50) is sufficiently inserted into adaptor (80), guide rail (75) no longer contacts stop (87), thereby allowing resilient arm (89) and stop (87) to return upwardly to a relaxed position. Stop (87) is positioned to block tissue container (50) from inadvertently exiting adaptor (80) by abutting against guide rail (75).

Figure 8D:
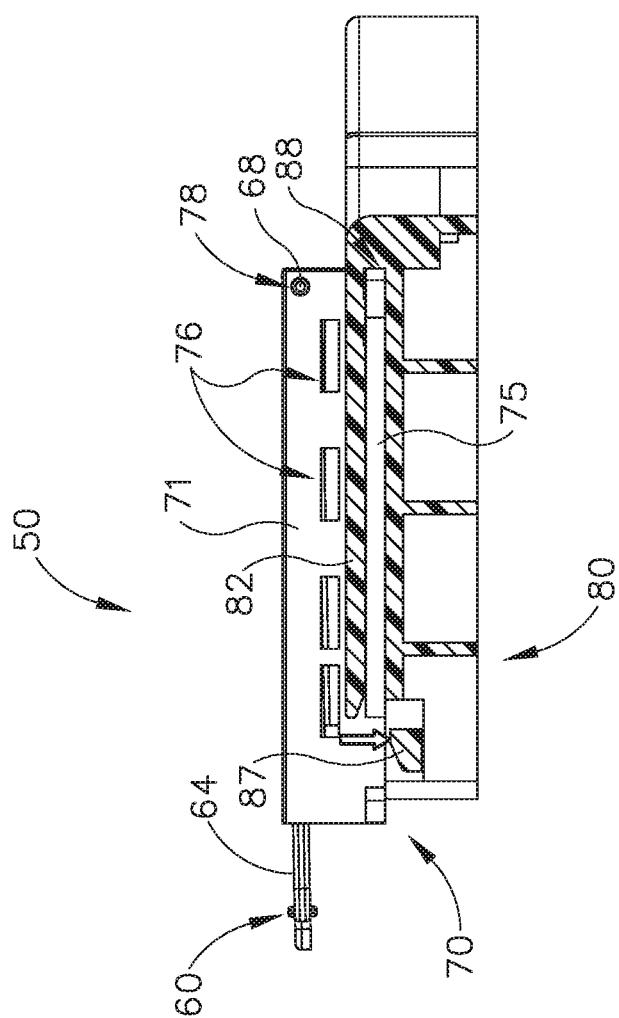
FIG. 8D depicts a side cross-sectional view, taken along line 8-8 of FIG. 7, of the tissue container of FIG. 3 coupled with the adaptor of FIG. 6 but with a stop of the adaptor being deflected to enable decoupling of the tissue container from the adaptor.
Figure 8E:
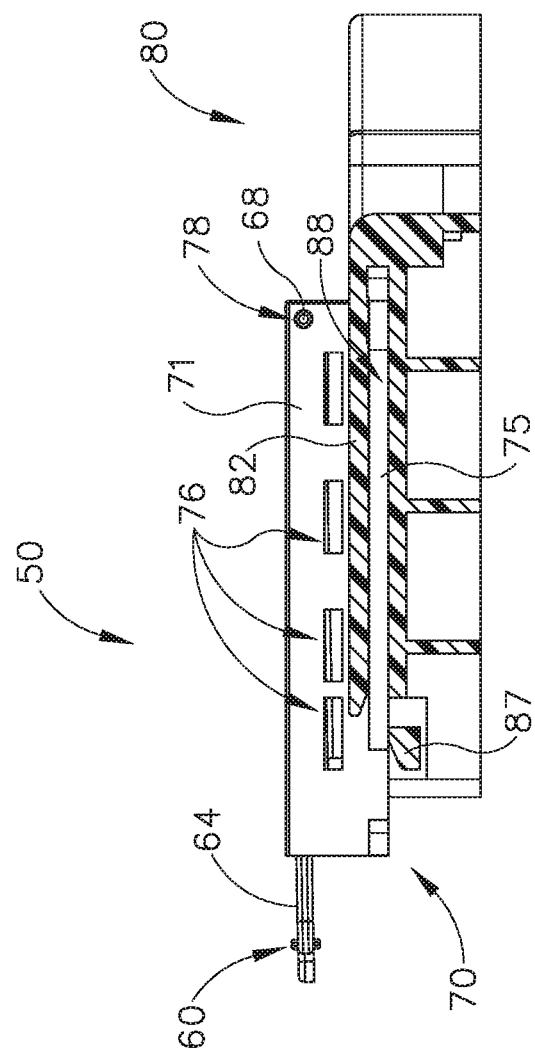
FIG. 8E depicts a side cross-sectional view, taken along line 8-8 of FIG. 7, of the tissue container of FIG. 3 being decoupled from the adaptor of FIG. 6.
Figure 8F:
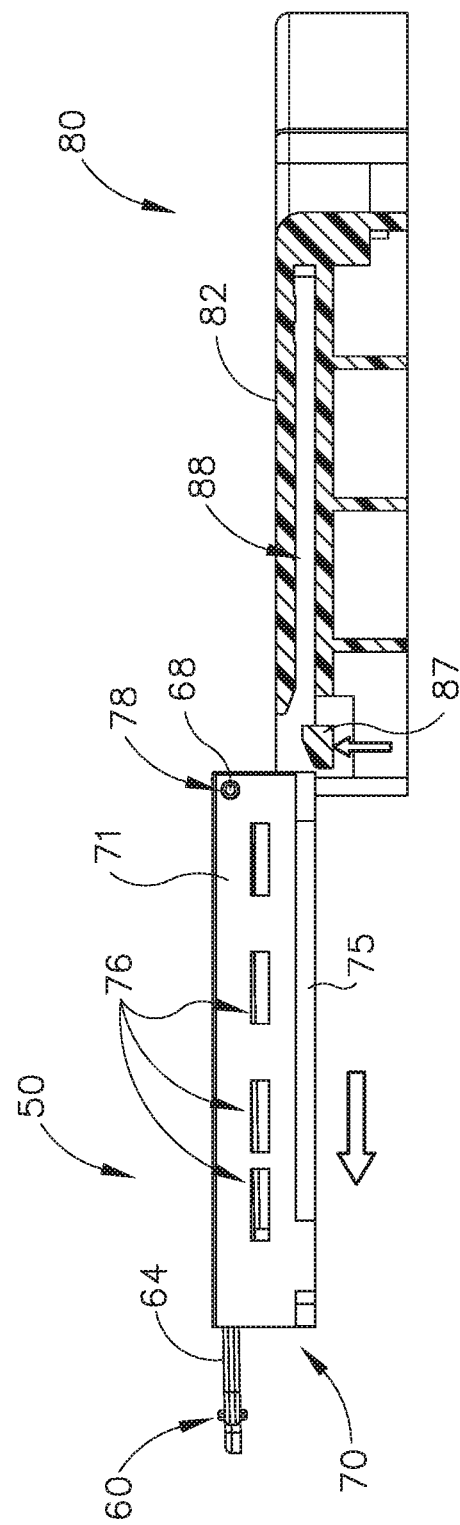
FIG. 8F depicts a side cross-sectional view, taken along line 8-8 of FIG. 7, of the tissue container of FIG. 3 decoupled from the adaptor of FIG. 6.
Figure 9:
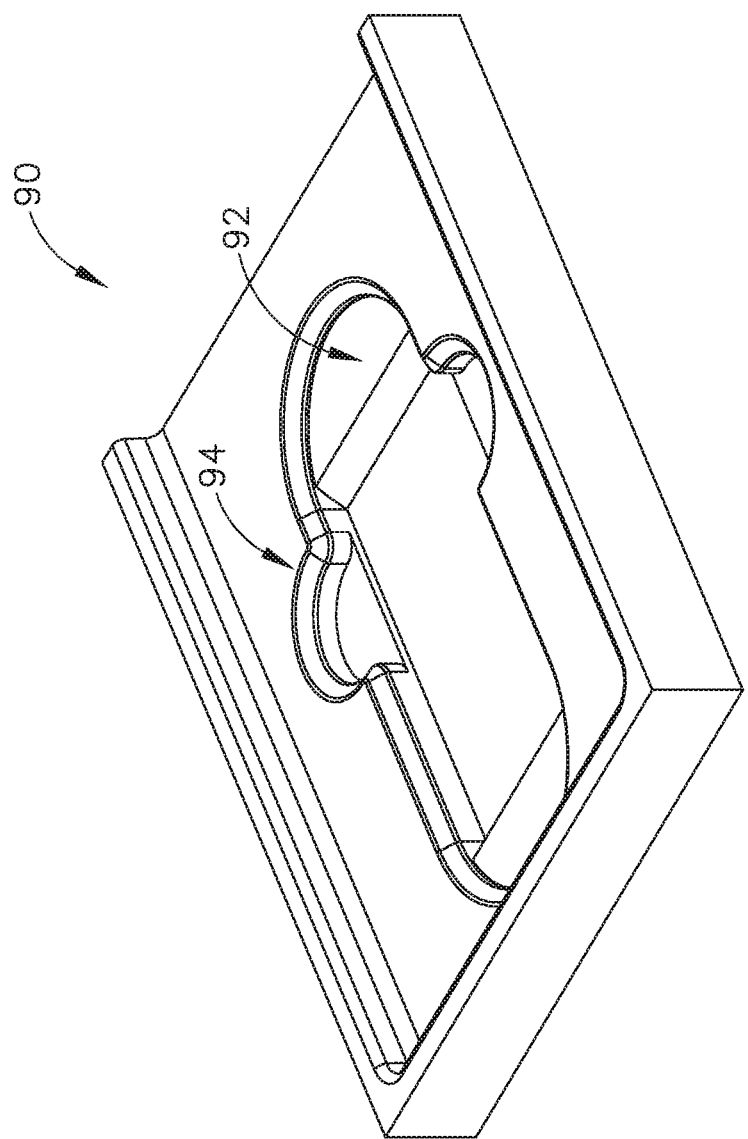
FIG. 9 depicts a perspective view of an exemplary radiograph drawer that may be used to receive the adaptor of FIG. 6.

If an operator desires to remove tissue container (50) from adaptor (80), an operator may force stop (87) into the downward position shown in FIG. 8D by pushing resilient arm (89) downwardly. As shown between FIG. 8D and FIG. 8E, with stop (87) in the downward position, tissue container (50) is free to be removed from adaptor (80) since stop (87) no longer blocks sliding movement of guide rail (75). As shown in FIG. 8E, as tissue container (50) is being removed from adaptor (80), guide rail (75) deflects resilient arm (89) and stop (87) toward container recess (86). As shown in FIG. 8F, once tissue container (50) is sufficiently removed from adaptor (80), resilient arm (89) and stop (87) snap upwardly to the relaxed position. It should therefore be understood that an operator may selectively couple and decouple tissue container (50) with adaptor (80).

As can be seen in FIG. 5, one guide rail (75) is shorter than the other. The shorter guide rail (75) should be inserted into guide slot (88) that is adjacent to stop (87). As will be described in greater detail below, the shorter guide rail (75) is dimensioned to travel on top of stop (87) as guide rails (75) are inserted into guide slots (88). Once the shorter guide rail (75) is completely inserted with guide slot (88), stop (87) is configured to prevent inadvertent removal of tissue container (50) from adaptor (80). In particular, the end of the shorter guide rail (75) adjacent to stop (87) abuts against stop (87). If tissue container (50) is inserted such that the longer guide rail (75) is within guide slot (88) adjacent to stop (87), stop (87) will interfere with guide rail (75) such that tissue container (50) does not properly rest within container recess (86). Therefore, tissue container (50) may only be inserted into adaptor in one direction. This may help ensure that tissue container (50) is placed in a consistent location relative to adaptor (80). In other words, stop (87) may serve as a poka-yoke feature in addition to serving as a retention feature.

As will be described in greater detail below, locating feature (84) is dimensioned to mate with a complementary recess of drawer (90) such that adaptor (80) may only insert into drawer (90) in a single orientation. This may help ensure that adaptor (80) and therefore tissue container (50) is consistently inserted within radiograph machine (100). Thus, locating feature (84) may also serve as a poke-yoke feature.

In addition to, or in lieu of, the foregoing, at least a portion of adaptor (80) may be constructed and operable in accordance with at least some of the teachings of U.S. Pub. No. 2014/0275999, entitled "Biopsy Device," published Sep. 18, 2014, the disclosure of which is incorporated by reference herein. Various suitable ways in which the teachings herein may be combined with the teachings of U.S. Pub. No. 2014/0275999 will be apparent to those of ordinary skill in the art.

IV. Exemplary Radiograph Machine

As shown in FIGS. 11A-11D, radiograph machine (100) includes a radiograph drawer (90) that is operable to transition between an open and closed position. In FIGS. 11A-11D, radiograph drawer (90) is shown in the open position. Radiograph drawer (90) includes an adaptor recess (92) and a locator recess (94). Radiograph drawer (90) is slidably received within a drawer opening (102) of radiograph machine (100). When drawer (90) is in the closed position, radiograph machine (100) is operable to capture x-ray images of tissue samples that are located in radiograph drawer (90) using known components and techniques. By way of example only, radiograph machine (100) may comprise a CoreVision® Specimen Radiography System manufactured by Faxitron Bioptics, LLC of Tucson, Ariz. Alternatively, any other suitable kind of radiograph machine (100) may be used, with or without adaptor (80), as will be apparent to those of ordinary skill in the art in view of the teachings herein Adaptor recess (92) is dimensioned to house adaptor (80), while locator recess (94) is dimensioned to house locating feature (84). In particular, an operator may place adaptor (80), coupled with tissue container (50), within radiograph drawer (90) by aligning locating feature (84) with locator recess (94) and dropping adaptor (80) within both adaptor recess (92) and locator recess (94). While in the current example, adaptor (80) is used to properly couple tissue container (50) with radiograph drawer (90), this is merely optional. In some instances, tissue container (50) may be properly positioned in radiograph drawer (90) without an adaptor (80). Radiograph drawer (90) may be configured to directly receive tissue container (50) such that tissue container (50) is consistently placed within radiograph drawer (90).

V. Exemplary Tissue Handling and Transport Protocol

Figure 10:
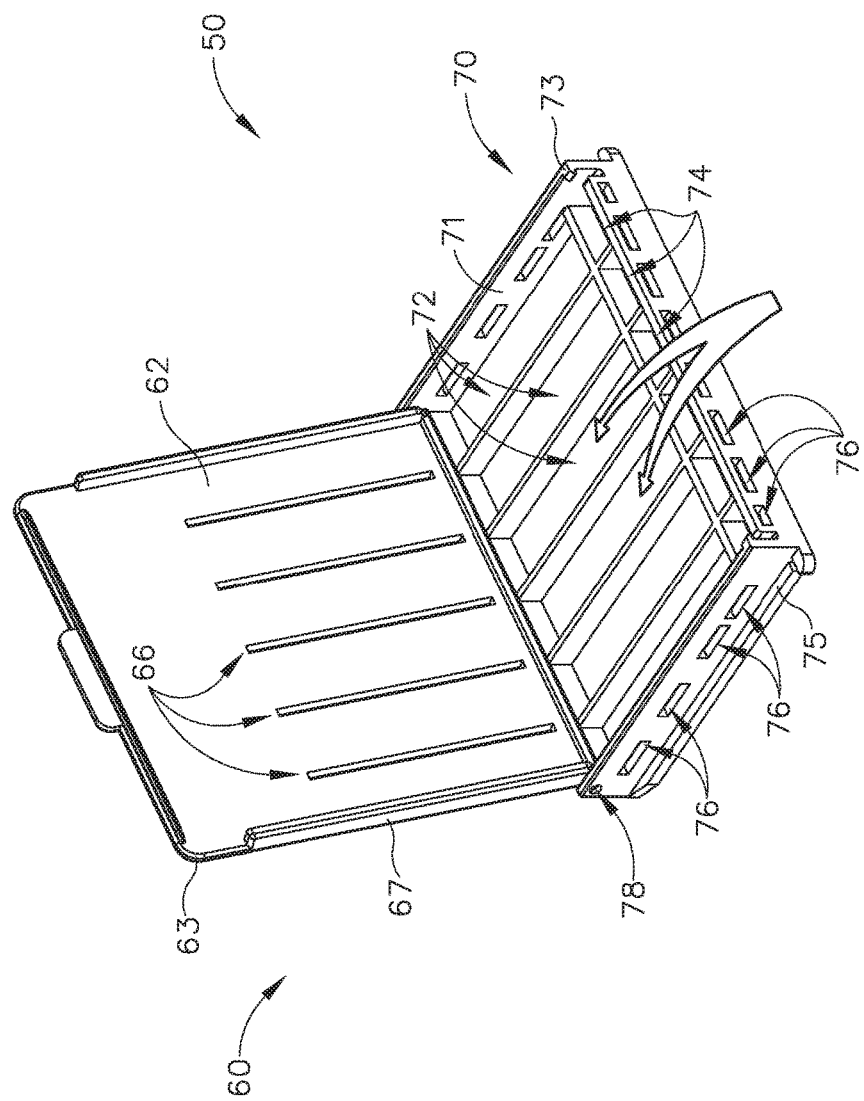
FIG. 10 depicts a perspective view of the tissue container of FIG. 3, in an open configuration, where the tissue container is being loaded with tissue samples.
Figure 11B:
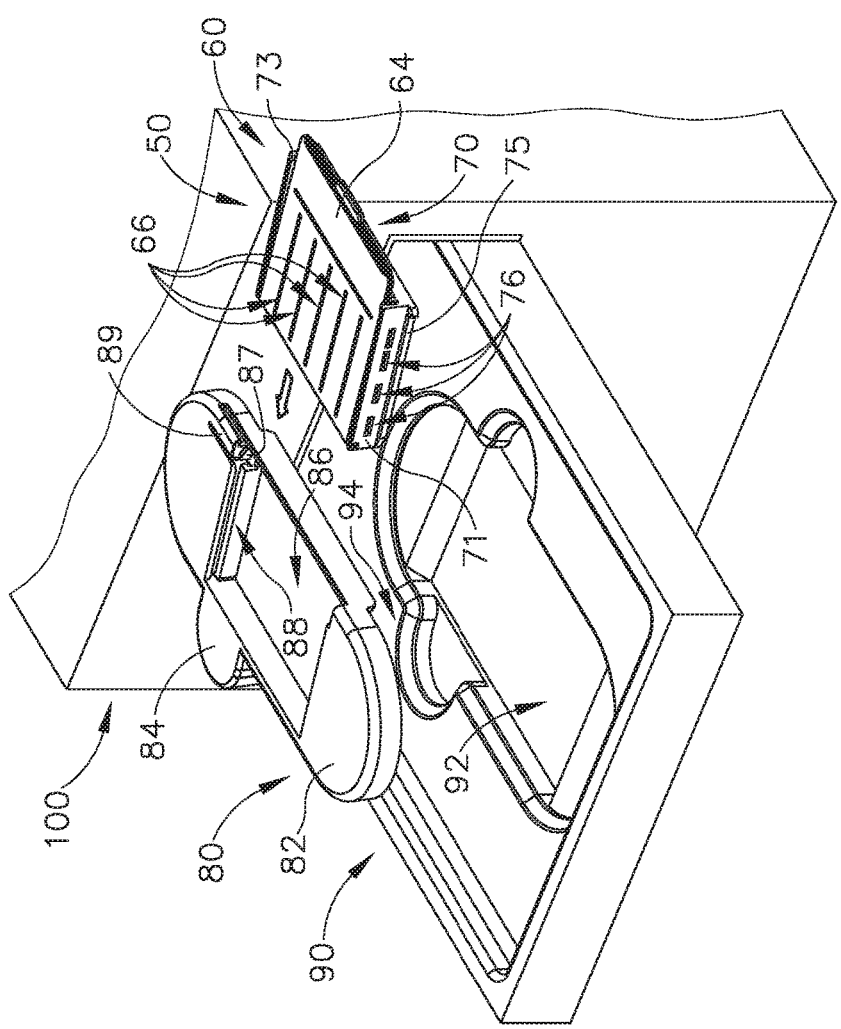
FIG. 11B depicts a perspective view of the adaptor of FIG. 6 and the container of FIG. 3, uncoupled with each other, positioned over the radiograph drawer of FIG. 9, where the radiograph drawer is in the open configuration relative to the radiograph machine of FIG. 11A.
Figure 11C:
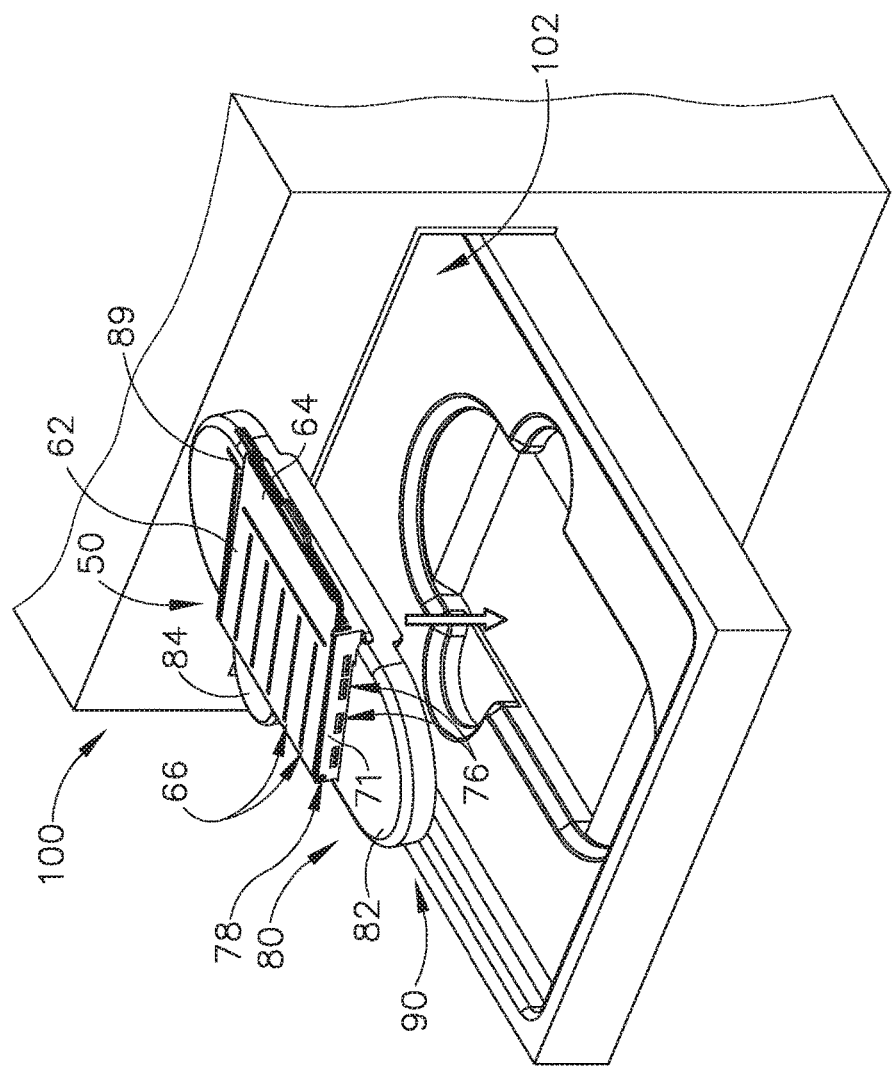
FIG. 11C depicts a perspective view of the adaptor of FIG. 6 and the tissue container of FIG. 3, coupled with each other, positioned over the radiograph drawer of FIG. 9, where the radiograph drawer is in the open configuration relative to the radiograph machine of FIG. 11A.
Figure 11D:
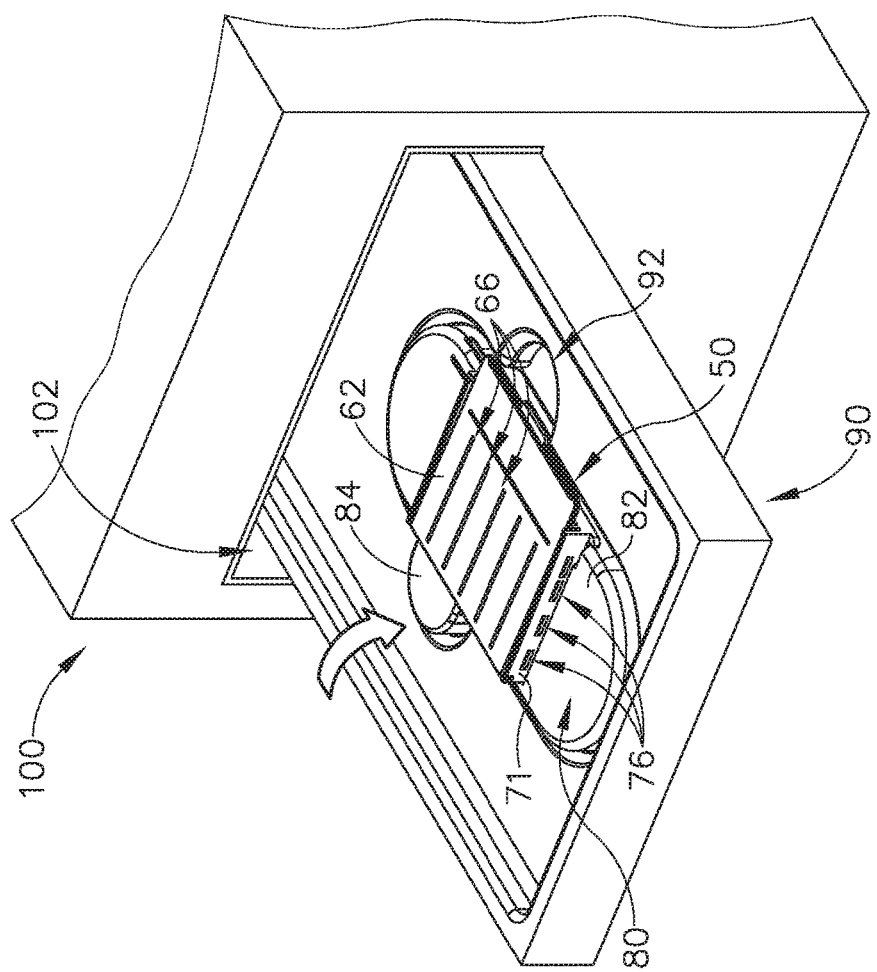
FIG. 11D depicts a perspective view of the combination of the tissue container of FIG. 3 and the adaptor of FIG. 6 inserted into the radiograph drawer of FIG. 9, where the radiograph drawer is in the open configuration relative to the radiograph machine of FIG. 11A.
Figure 12:
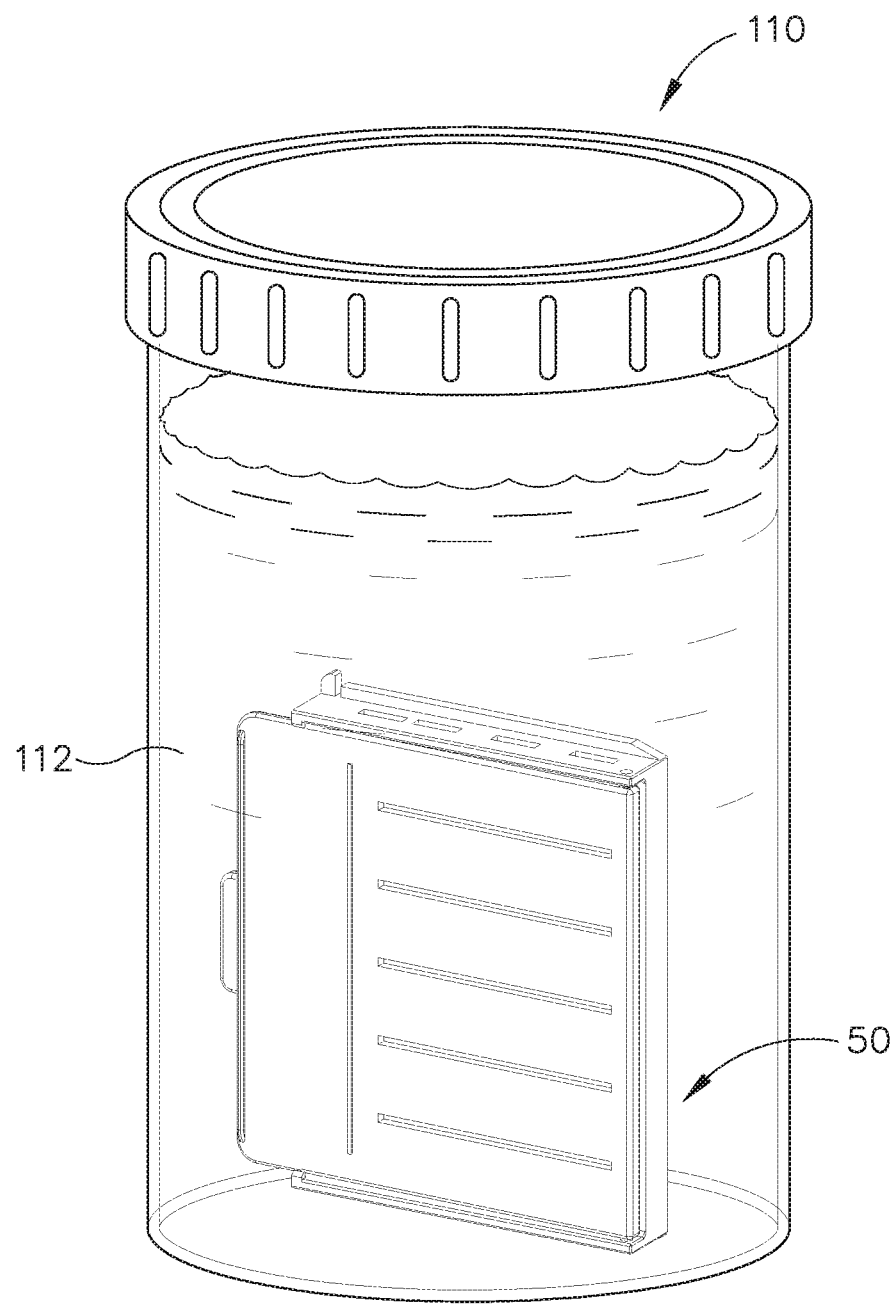
FIG. 12 depicts a perspective view of the tissue container of FIG. 3 inserted into a jar filled with formalin.

FIGS. 10-12 depicts an exemplary use of tissue container (50), adaptor (80), radiograph drawer (90), and radiograph machine (100) to individually analyze and transport tissue samples without the need of direct tissue handling in-between analyzing and transporting tissue samples.

FIG. 10 shows arrows, representing individual tissue samples, being loaded into separated reservoirs (72) of tissue container (50) while lid (60) is in the open configuration. It should be understood that an operator may obtain tissue samples through use of biopsy device (10), and take tissue samples previously lumped together within tissue basket (46) of tissue sample holder (40) and individually place them into separate respective reservoirs (72). As noted above, this may be done using forceps and/or any other suitable instrumentation to grasp and manipulate the tissue samples. Once an operator has loaded the desired amount of tissue samples into tissue container (50), an operator may close lid (60) as described above.

After tissue container (50) has been loaded, an operator may prepare radiograph machine (100) for receiving adaptor (80) and tissue container (50). In particular, FIG. 11A shows radiograph drawer (90) slidably coupled within drawer opening (102) of radiograph machine (100). Drawer (90) is outside of radiograph machine (100), in an open position, and is therefore ready to receive adaptor (80) and tissue container (50).

After preparing radiograph machine (100) for receiving tissue container (50), adaptor (80) and tissue container (50) are prepared for insertion into radiograph drawer (90) of radiograph machine (100). In particular, FIG. 11B shows adaptor (80) and tissue container (50), while separated, placed above drawer (90). As described above, the shorter guide rail (75) is aligned to be inserted within guide slot (88) adjacent to stop (87). Aligning the shorter guide rail (75) with guide slot (88) adjacent to stop (87) may help ensure proper placement of tissue container (50) relative to adaptor (80). After an operator aligns adaptor (80) and tissue container (50), tissue container (50) can be slid into adaptor (80). As described above, stop (89) is initially deflected away by shorter guide rail (75) before snapping back into the relaxed position to lock tissue container (50) within adaptor (80). With adaptor (80) and tissue container (50) coupled, adaptor (80) may now be placed within drawer (90).

With tissue container (50) and adaptor (80) coupled together, an operator may next load the combination of adaptor (80) and tissue container (50) into drawer (90). In particular, FIG. 11C shows a loaded tissue container (50) coupled with adaptor being loaded within drawer (90). As described above, locating feature (84) is aligned within locating recess (94). Aligning locating feature (84) with locating recess (94) may help ensure proper placement of adaptor (80) relative to drawer (90).

FIG. 11D shows tissue container (50) properly loaded into adaptor (80) such that stop (87) effectively holds tissue sample tray tissue container (50) in place as describe above. At this point, tissue container (50) is properly inserted within drawer (90) of radiograph machine (100). While the foregoing process provides loading of tissue container (50) into adaptor (80) before adaptor (80) has been loaded in drawer (90), some alternative processes may load tissue container (50) into adaptor (80) after loading adaptor (80) tissue container (50) into drawer (90).

After reaching the state shown in FIG. 11D, drawer (90) may then slide within drawer opening (102) of radiograph machine (100) to the closed position. With drawer (90) closed, radiograph machine (100) may then be operated to capture one or more x-ray images of the tissue contained in tissue container (50). Radiograph machine (100) may also perform any other suitable processing based on the x-ray data (e.g., automatically highlight potential calcifications, and/or other anomalies, etc.).

After radiograph machine (100) has performed tissue imaging (and, optionally, tissue analysis), drawer (90) may be opened again and then tissue container (50) may be removed from adaptor (80). Tissue container (50) may then be placed into a tissue sample jar (110) filled with formalin (112) as shown in FIG. 12. Once tissue container (50) is placed into tissue sample jar (110) filled with formalin (112), vents (66) will allow reservoirs (72) of tissue container (50) to also fill with formalin (112), thereby helping preserve the tissue samples during the transportation process. As described above, it should be understood that during the process of analysis and transportation, tissue samples taken by biopsy device (10) and removed from lump collection of tissue basket (46) are organized, analyzed, and transported without further outside contact after organization within tissue container (50).

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

I claim:

1. An apparatus for individually storing multiple tissue samples separately from each other, the apparatus comprising:
   (a) a base defining a plurality of reservoirs, wherein a portion of the base defines a plurality of openings with each opening associated with a corresponding reservoir;
   (b) a lid configured to transition between an open configuration and a closed configuration, wherein the lid is configured to secure each tissue sample of the multiple tissue samples within a corresponding reservoir by enclosing each corresponding opening in the closed configuration;
   (c) a plurality of identification areas, wherein each identification area of the plurality of identification areas is associated with the base or the lid;

(d) a lock, wherein the lock is configured to selectively lock the lid against the base in the closed configuration; and (e) one or more vents, wherein the one or more vents are configured to enable entry of fluid into the reservoirs when the lid is in the closed configuration, wherein the one or more vents are sized sufficiently small to prevent exit of tissue samples from the reservoirs when the lid is in the closed configuration.

2. The apparatus of claim 1, wherein the lid is pivotally coupled to the base.

3. The apparatus of claim 2, wherein the lid includes a pair of pivot studs, wherein the base includes a corresponding pair of pivot holes.

4. The apparatus of claim 2, wherein the lid is pivotally coupled to the base via a living hinge.

5. The apparatus of claim 1, wherein the lock includes a resilient tab associated with the base.

6. The apparatus of claim 1, wherein each reservoir of the plurality of reservoirs includes an enclosed perimeter.

7. The apparatus of claim 1, wherein each identification area of the plurality of identification areas is directly adjacent to a corresponding reservoir in the plurality of reservoirs of the base.

8. The apparatus of claim 1, wherein each identification area of the plurality of identification areas coincides with a corresponding reservoir in the plurality of reservoirs.

9. The apparatus of claim 1, wherein the one or more vents include at least one vent formed in the lid.

10. The apparatus of claim 1, wherein the one or more vents include at least one vent formed in the base.

11. The apparatus of claim 1, further comprising an adaptor defining at least one guide slot, and a stop; wherein the base further includes at least one guide rail configured to be inserted into the at least one guide slot, wherein the stop and the guide rail are configured to selectively lock the adaptor with the base.

12. The apparatus of claim 11, wherein the adaptor includes a resilient arm associated with the stop, wherein the resilient arm is configured to deform from a first position to a second position in response to the at least one guide rail being inserted into the at least one guide slot, wherein the stop is configured to lock the base with the adaptor when the at least one guide rail is inserted into the at least one guide slot and the resilient arm is in the first position.

13. The apparatus of claim 12, wherein the resilient arm is configured to deform from the first position to the second position while the base is inserted within the adaptor to unlock the base from the adaptor.

14. The apparatus of claim 11, further comprising a radiograph drawer defining an adaptor recess and a locator recess, wherein the adaptor further includes a locating feature, wherein the adaptor recess is configured to house the adaptor, wherein the locator recess is configured to house the locating feature in order to align the adaptor relative to the radiograph drawer.

15. The apparatus of claim 1, wherein the lid includes a pair of side rails dimensioned to be positioned adjacent with an outer perimeter of a corresponding reservoir when the lid is in the closed configuration.

16. The apparatus of claim 1, further comprising a plurality of sidewalls extending from a portion of the base, wherein the plurality of sidewalls define each reservoir of the plurality of reservoirs.

17. The apparatus of claim 1, wherein each identification area includes a visual identifier, wherein each visual identifier is associated with a reservoir such that each visual identifier is configured to identify an associated reservoir.

18. An apparatus for individually storing multiple tissue samples separately from each other, the apparatus comprising:

(a) a container including:
  (i) a base defining a plurality of reservoirs and a plurality of identification areas, wherein each reservoir in the plurality of reservoirs is at least partially defined by a perimeter, wherein each perimeter defines an opening corresponding to each reservoir,
  (ii) a lid configured to pivot between an open configuration and a closed configuration, wherein the lid is configured to cover each corresponding opening defined by each perimeter in the closed configuration, and
  (iii) a lock, wherein the lock is configured to selectively lock the lid against the base in the closed configuration; and (b) an adaptor configured to house the container in order to selectively couple the container with a radiograph drawer.

19. The apparatus of claim 18, wherein the lid is configured to extend past the base when the lid is in the closed configuration.

20. The apparatus of claim 19, wherein a portion of the lid extending past the base in the closed configuration defines a label area.

21. The apparatus of claim 18, wherein the container defines an exterior, wherein the container defines a vent configured to provide fluid communication from the exterior to at least one reservoir in the plurality of reservoirs.

22. An apparatus for individually storing multiple tissue samples separately from each other, the apparatus comprising:

(a) a base defining a plurality of reservoirs and a plurality of identification areas, wherein each identification area corresponds to a reservoir in the plurality of reservoirs, wherein each reservoir in the plurality of reservoirs including a wall, wherein a portion of each wall defines an opening corresponding to each reservoir; and (b) a lid formed of transparent material, wherein the lid is configured to transition between an open configuration and a closed configuration, wherein the lid is configured to lay adjacent to each corresponding opening in the closed configuration, wherein the lid is configured to secure the multiple tissue samples within a corresponding reservoir in the closed configuration, wherein each corresponding reservoir is configured to be in fluid communication with an exterior of the apparatus when the lid is in the closed configuration.

23. A system for storing and transporting multiple tissue sample, the system comprising:

(a) a tissue container, the tissue container including:
  (i) a base defining a plurality of reservoirs, wherein a portion of the base defines a plurality of openings with each opening associated with a corresponding reservoir,
  (ii) a lid configured to transition between an open configuration and a closed configuration, wherein the lid is configured to secure one or more tissue samples within one or more reservoirs by enclosing each reservoir in the closed configuration,
  (iii) a plurality of identification areas, wherein each identification area of the plurality of identification areas is associated with the base or lid, (iii) a lock, wherein the lock is configured to selectively lock the lid against the base in the closed configuration, and
(iv) one or more vents configured to enable entry of fluid into the reservoirs when the lid is in the closed configuration, wherein the one or more vents are sized sufficiently small to prevent exit of tissue samples from the reservoirs when the lid is in the closed configuration; and
(b) a transport jar filled with formalin, wherein the transport jar is configured to enclose the tissue container therein for transport of the tissue container.

24. The system of claim 23, wherein the lock includes one or more tabs configured to secure the lid in the closed configuration to the base.

25. The system of claim 23, wherein the one or more vents includes a plurality of vents arranged on a first side of the base and a plurality of vents arranged on a second side of the base, wherein the first side is opposite of the second side.

26. The system of claim 23, wherein the transport jar includes a cap configured to seal the tissue container within a cavity of the transport jar.

\* \* \* \* \*